United States Patent
Akiba et al.

(10) Patent No.: US 10,258,794 B2
(45) Date of Patent: Apr. 16, 2019

(54) ELECTRICAL STIMULATION DEVICE, TRAINING APPARATUS, AND ELECTRICAL STIMULATION METHOD

(71) Applicants: SYSTEM INSTRUMENTS CO., LTD., Hachioji-shi, Tokyo (JP); The University of Electro-Communications, Chofu-shi, Tokyo (JP)

(72) Inventors: Takeshi Akiba, Tokyo (JP); Hiroshi Yokoi, Tokyo (JP)

(73) Assignees: SYSTEM INSTRUMENTS CO., LTD., Tokyo (JP); THE UNIVERSITY OF ELECTRO-COMMUNICATIONS, Tokyo (JP)

( * ) Notice: Subject to any disclaimer, the term of this patent is extended or adjusted under 35 U.S.C. 154(b) by 133 days.

(21) Appl. No.: 15/126,879

(22) PCT Filed: Jul. 23, 2014

(86) PCT No.: PCT/JP2014/069429
§ 371 (c)(1),
(2) Date: Sep. 16, 2016

(87) PCT Pub. No.: WO2016/013067
PCT Pub. Date: Jan. 28, 2016

(65) Prior Publication Data
US 2017/0100586 A1 Apr. 13, 2017

(51) Int. Cl.
*A61N 1/36* (2006.01)
*A61H 1/02* (2006.01)
(Continued)

(52) U.S. Cl.
CPC ........ *A61N 1/36003* (2013.01); *A61B 5/0408* (2013.01); *A61B 5/1118* (2013.01);
(Continued)

(58) Field of Classification Search
CPC ..................... A61N 1/36003; A61N 1/36014
See application file for complete search history.

(56) References Cited

U.S. PATENT DOCUMENTS 4,919,139 A * 4/1990 Brodard ................... A61N 1/08
607/59
5,016,635 A * 5/1991 Graupe ................ A61B 5/0488
600/546

(Continued)

FOREIGN PATENT DOCUMENTS

| CN | 101041101 A | 9/2007 |
| JP | 2004-209040 A | 7/2004 |

(Continued)

OTHER PUBLICATIONS

Jan. 23, 2018 Office Action issued in Japanese Patent Application No. 2016-535572.
(Continued)

*Primary Examiner* — George R Evanisko
(74) *Attorney, Agent, or Firm* — Oliff PLC

(57) ABSTRACT

Provided is an electrical stimulation device including a first to fourth electrodes, and an electrical stimulation generation section which supplies an electrical stimulation signal to each of the first to fourth electrodes. The electrical stimulation generation section supplies, to the first and second electrodes, an electrical stimulation signal according to a first stimulation pattern, and supplies, to the third and fourth electrodes, an electrical stimulation signal according to a second stimulation pattern. The first stimulation pattern is set so that an electrical stimulation signal for changing
(Continued)

stimulation intensity according to a first waveform is supplied to the first electrode, and an electrical stimulation signal for changing stimulation intensity according to a second waveform is supplied to the second electrode, the second waveform being increased and decreased in conjunction with the first waveform. The second stimulation pattern is set so that an electrical stimulation signal for changing stimulation intensity according to a third waveform is supplied to the third electrode, and an electrical stimulation signal for changing stimulation intensity according to a fourth waveform is supplied to the fourth electrode, the fourth waveform being increased and decreased in conjunction with the third waveform. The electrical stimulation generation section alternately performs electrical stimulation of the first stimulation pattern and electrical stimulation of the second stimulation pattern.

4 Claims, 22 Drawing Sheets

(51) Int. Cl.

| | | |
|---|---|---|
| *A61N 1/04* | (2006.01) | |
| *A61B 5/0408* | (2006.01) | |
| *A61B 5/11* | (2006.01) | |
| *A61B 5/22* | (2006.01) | |
| *A61N 1/32* | (2006.01) | |
| *G06F 19/00* | (2018.01) | |
| *A63B 21/06* | (2006.01) | |
| *A63B 21/00* | (2006.01) | |
| *A63B 23/035* | (2006.01) | |
| *A63B 23/04* | (2006.01) | |

(52) U.S. Cl.
CPC ............ *A61B 5/1124* (2013.01); *A61B 5/224* (2013.01); *A61H 1/0237* (2013.01); *A61N 1/0452* (2013.01); *A61N 1/32* (2013.01); *A61N 1/36* (2013.01); *A61N 1/36014* (2013.01); *G06F 19/00* (2013.01); *G06F 19/3481* (2013.01); *A61B 2562/0219* (2013.01); *A61B 2562/0247* (2013.01); *A63B 21/00065* (2013.01); *A63B 21/06* (2013.01); *A63B 21/151* (2013.01); *A63B 21/154* (2013.01); *A63B 21/4034* (2015.10); *A63B 21/4045* (2015.10); *A63B 21/4047* (2015.10); *A63B 23/03508* (2013.01); *A63B 23/0405* (2013.01); *A63B 2213/004* (2013.01); *A63B 2220/10* (2013.01); *A63B 2220/30* (2013.01); *A63B 2220/40* (2013.01); *A63B 2220/56* (2013.01); *A63B 2220/803* (2013.01); *A63B 2220/836* (2013.01); *A63B 2230/60* (2013.01)

(56) References Cited

U.S. PATENT DOCUMENTS

| | | | | |
|---|---|---|---|---|
| 5,300,096 | A | * | 4/1994 | Hall .................. A61N 1/36003 607/48 |
| 5,562,718 | A | * | 10/1996 | Palermo ............ A61N 1/36021 607/46 |
| 6,507,757 | B1 | | 1/2003 | Swain et al. |
| 2007/0142876 | A1 | | 6/2007 | Sakagami et al. |
| 2013/0137549 | A1 | | 5/2013 | Hamada et al. |
| 2014/0113261 | A1 | | 4/2014 | Akiba |
| 2015/0148866 | A1 | * | 5/2015 | Bulsen ............... A61N 1/36014 607/48 |

FOREIGN PATENT DOCUMENTS

| | | |
|---|---|---|
| JP | 2006-020947 A | 1/2006 |
| JP | 2008-067917 A | 3/2008 |
| JP | 2011-143061 A | 7/2011 |
| JP | 2013-244101 A | 12/2013 |
| WO | 2012/168999 A1 | 12/2012 |
| WO | 2013/153635 A1 | 10/2013 |
| WO | 2014/000107 A1 | 1/2014 |

OTHER PUBLICATIONS

Feb. 2, 2018 Search Report issued in European Patent Application No. 14898205.1.
Oct. 21, 2014 International Search Report issed in International Patent Application No. PCT/JP2014/069429.
Feb. 2, 2017 International Preliminary Report on Patentability issued in International Patent Application No. PCT/JP2014/069429.
Oct. 12, 2018 Office Action issued in Chinese Patent Application No. 201480080237.3.

* cited by examiner

ELECTRICAL STIMULATION DEVICE, TRAINING APPARATUS, AND ELECTRICAL STIMULATION METHOD

FIELD

The present invention relates to an electrical stimulation device, a training apparatus, and an electrical stimulation method.

BACKGROUND

It is difficult for people with weak muscles, people with cerebrovascular disease, or the like, to individually train muscle strength required for performing walking motion, and the like. Conventionally, for example, a training apparatus using electrical stimulation to assist exercise is known from PTLs 1 and 2 described below. In paragraph 0075 of PTL 1, the relationship between bending and stretching exercises and an energization of an electrical stimulation device is described. Further, in paragraph 0106 of PTL 1, it is described that electrical stimulation intensity may not be fixed. In paragraph 0018 of PTL 2, it is described that electrical stimulation is applied to muscles to make the muscles contract. Further, in paragraph 20 of the PTL 2, it is described that electrodes of an electrical stimulation device are attached to thigh flexor muscles and quadriceps femoris muscles.

CITATION LIST

Patent Literature

[PTL 1] JP 2008-67917 A
[PTL 2] JP 2004-209040 A

SUMMARY

Technical Problem

However, the techniques discussed in the above-described patent literatures provide an electrical stimulation method for simply bending and stretching the leg by attaching electrodes to thigh portions. From a viewpoint of performing muscle strength training necessary for complex motions such as, for example, walking, performed in everyday life, the prior art still has room to be improved.

The present invention has been made in order to solve the above-described problem. An object of the present invention is to provide an electrical stimulation device, a training apparatus, and an electrical stimulation method, with which practical muscle strength training can be performed.

Solution to Problem

A first invention is an electrical stimulation device which includes a first electrode, a second electrode, a third electrode, and a fourth electrode, and an electrical stimulation generation section. The electrical stimulation generation section alternately performs first electrical stimulation by the first electrode and the second electrode, and second electrical stimulation by the third electrode and the fourth electrode, to thereby supply an electrical stimulation signal to each of the first electrode, the second electrode, the third electrode, and the fourth electrode.

A second invention is an electrical stimulation device which includes a plurality of electrodes, and an electrical stimulation generation section that supplies an electrical stimulation signal to each of the plurality of electrodes. the plurality of electrodes includes a first electrode and a second electrode. The electrical stimulation generation section supplies, to the first electrode, an electrical stimulation signal for changing stimulation intensity according to a first waveform, and supplies, to the second electrode, an electrical stimulation signal for changing stimulation intensity according to a second waveform. The first waveform reaches a first peak due to increase in amplitude thereof and decreases after lapse of a pre-set first section during which the first waveform is kept at the first peak. The second waveform is generated to reach a second peak after the first waveform reaches the first peak, and decreases after reaching the second peak.

A third invention is a training apparatus which includes an exercise detection section which detects an exercise state, and the electrical stimulation device according to the first invention or the second invention. The electrical stimulation device includes the plurality of electrodes, and the electrical stimulation generation section which supplies an electrical stimulation signal to each of the electrodes. When the exercise state coincides with an exercise state set beforehand, the training apparatus feeds back the output signal of the exercise detection section to the electrical stimulation generation section, to adjust the output of the electrical stimulation generation section.

The fourth invention is an electrical stimulation method which includes: promoting exercise of bending a leg; supplying a first electrical stimulation signal to a first portion of a lower thigh portion to plantar flex an ankle in conjunction with the bending; promoting exercise of extending the leg after the bending; and supplying a second electrical stimulation signal to a second portion of the lower thigh portion to dorsiflex the ankle in conjunction with the extension. Electrical stimulation by the first electrical stimulation signal associated with the bending, and electrical stimulation by the second electrical stimulation signal associated with the extension are alternately performed.

Advantageous Effects of Invention

With the present invention, it is possible to perform practical muscle strength training.

Other objects, other features and other effects of the present invention will become apparent from the following description.

DESCRIPTION OF EMBODIMENTS

Figure 1:
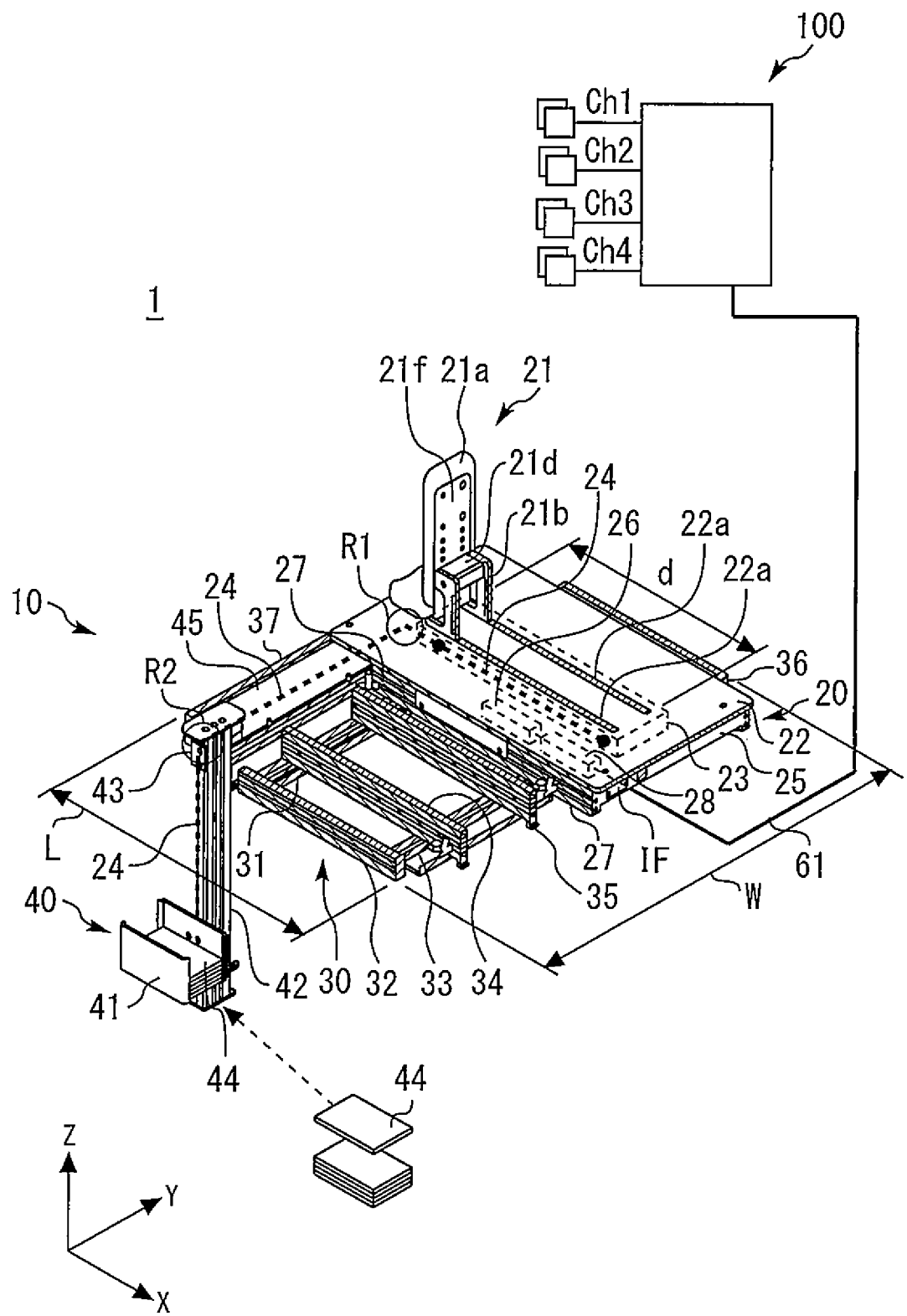
FIG. 1 is a perspective view showing a training apparatus according to an embodiment of the present invention.

It is difficult for people with cerebrovascular disease or people with weak muscles to individually train muscle strength required for practicing exercise, such as standing up, sitting down, squatting, standing, walking, and running. In order to increase muscle strength of these people as targets, a training apparatus 1 of a present embodiment is suitably used. In the present embodiment, in the state where an exercising person 2 lies on a bed, or the like, the exercising person 2 performs leg press in which a light load is applied to a leg 3 or is not applied to the leg 3 while electrical stimulation is attached to the leg 3. The training apparatus 1 is provided with an exercise apparatus 10 and an electrical stimulation device 100, and the exercise apparatus 10 is suitable for the leg press. However, the present invention is not limited to the embodiment using the exercise apparatus 10, but may also be used an apparatus used for performing other training other than leg press.

The Configuration of the Training Apparatus According to the Embodiment of the Present Invention.

[Overall Configuration of Training Apparatus]

Figure 2:
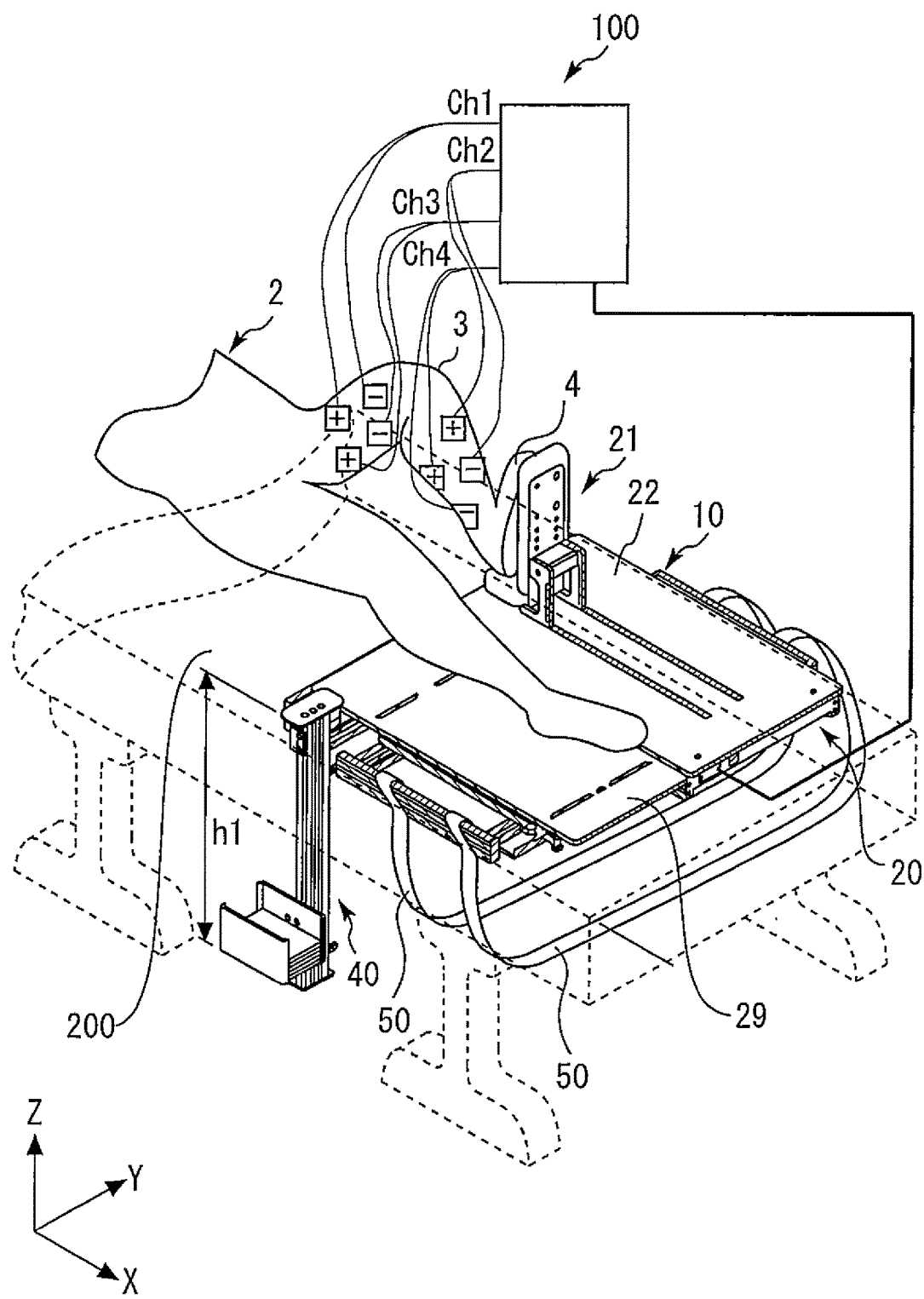
FIG. 2 is a perspective view showing the training apparatus according to the embodiment of the present invention.

FIG. 1 is a perspective view showing a training apparatus 1 according to an embodiment of the present invention. FIG. 1 also shows an XYZ orthogonal coordinate system. Preferably, it is assumed that Z-axis coincides with the vertical direction, and that XY plane coincides with the horizontal surface. FIG. 2 shows a state where the training apparatus 1 is used. The training apparatus 1 is provided with the exercise apparatus 10 and the electrical stimulation device 100. The exercise apparatus 10 is provided with an exercise detection section 20. The exercise detection section 20 is provided with a pedal section 21 for performing leg press, and an encoder 26 for detecting the position of the pedal section 21. The pedal section 21 corresponds to a displacement section capable of performing reciprocating motion, and the encoder 26 corresponds to a sensor for detecting the moving state of the displacement section.

[Configuration and Operation of Exercise Apparatus]

FIG. 1 shows the exercise apparatus 10 according to the embodiment of the present invention. The exercise apparatus 10 is provided with a support body 30, the exercise detection section 20, a load generation section 40, and a transmission wire 24. The support body 30 is a structure body forming the skeleton of the exercise apparatus 10. The support body 30 is integrated with each of the components, such as the exercise detection section 20 and the load generation section 40, which are mounted to the exercise apparatus 10. The exercise detection section 20 can detect the exercise state by detecting the moving distance of the pedal section 21. The load generation section 40 can apply a load to hinder the movement of the pedal section 21, and the transmission wire 24 transmits the load.

(Support Body)

The support body 30 has a ladder shape formed by combining a plurality of frames 31, 32, 33, 34, 35, 36 and 37 formed by suitably using a lightweight metal material, such as aluminum. The long frames 31, 33 and 37 are arranged in parallel with each other to extend in the Y-axis direction. The support body 30 has the width W and the length L as the external dimensions thereof.

(Exercise Detection Section)

The exercise detection section 20 is provided with a first rail 23, the pedal section 21, and the encoder 26, which are housed in a case 25. The case 25 is detachably attached to the support body 30 by case fixtures 27. A cover 22 is attached to the case 25. Two slits 22a, each having the length d, are provided on the cover 22. The pedal section 21 can reciprocally move on the first rail 23, and the maximum moving distance of the pedal section 21 is the length d. It should be noted that, as shown in FIG. 2, a top plate 29 can be attached close to the cover 22. The case fixtures 27 can attach the case 25 at a plurality of positions along the width W direction of the support body 30. Thereby, the case is made to correspond to left and right legs of the exercising person 2. The pedal section 21 is attached to the first rail 23, and can be reciprocated in the direction of length L on the first rail 23 (in the X-axis direction in FIG. 1). Since the first rail 23 is linearly extended from the pedal section 21 on which a leg 4 is placed, the direction of motion can be regulated, so that linear motion with high reproducibility can be performed. The encoder 26, used as an example of the position sensor in the present embodiment, detects the position of the pedal section 21 on the first rail 23, and various known rotary encoders can be used as the encoder 26. Instead of the position sensor, the motion of the pedal section 21 may be detected with a speed sensor or an acceleration sensor.

Figure 3:
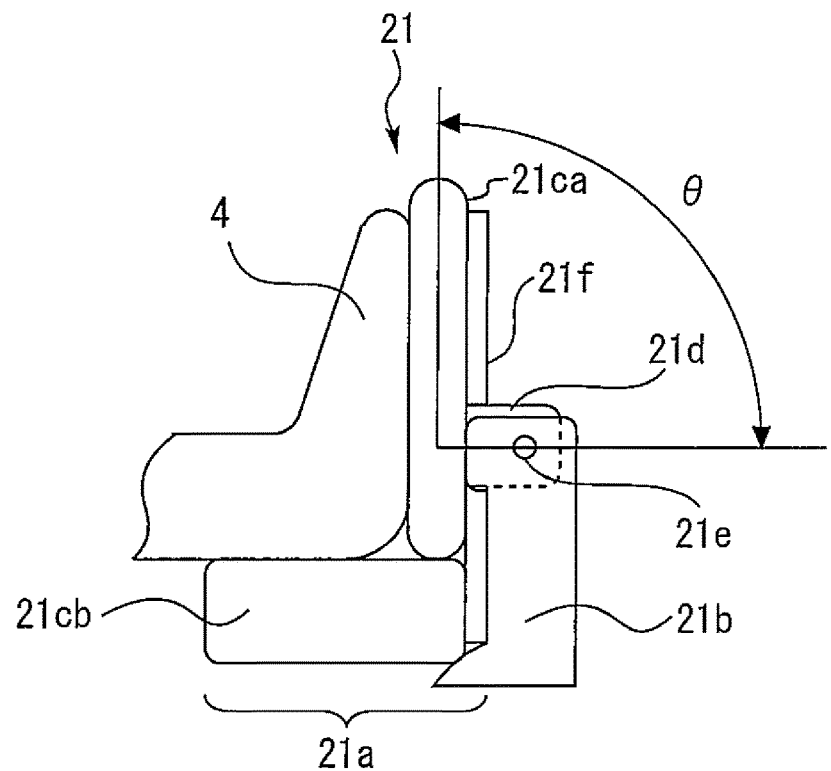
FIG. 3 is a view showing a pedal section of an exercise apparatus according to the embodiment of the present invention.
Figure 4:
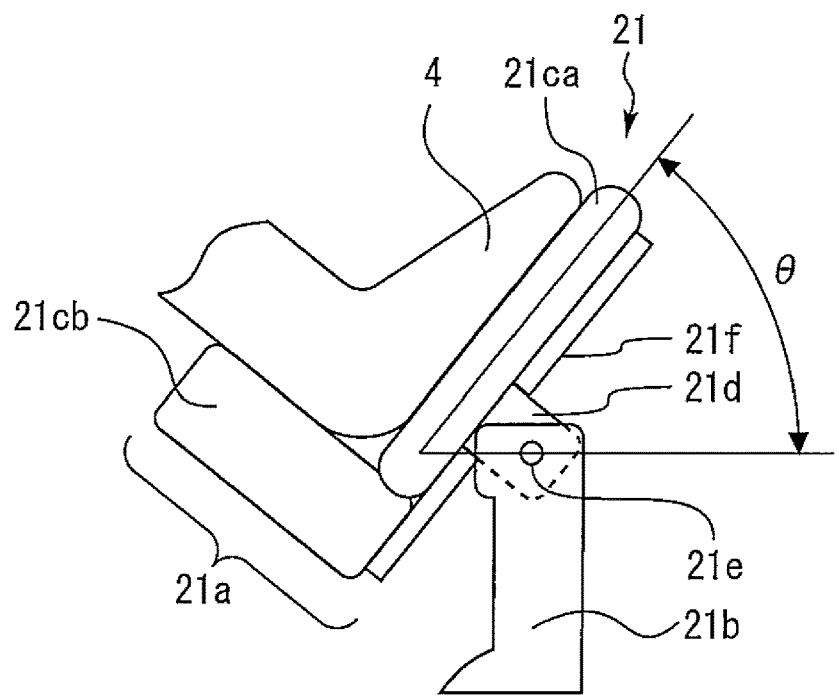
FIG. 4 is a view showing the pedal section of the exercise apparatus according to the embodiment of the present invention.

FIG. 3 and FIG. 4 are views showing the pedal section 21 of the exercise apparatus 10. The pedal section 21 is provided with a pedal body 21a, a movable metal fitting 21b, and a rotary shaft 21e. The pedal body 21a is provided with a mat 21ca on which the back side of the foot 4 is placed, a mat 21cb on which the heel of the foot 4 is placed, a plate 21f on the surface of which the mats 21ca and 21cb are fixed, and a metal fitting 21d provided on the back surface of the plate 21f. The pedal body 21a can be rotated about the rotary shaft 21e, and the angle θ of the pedal body 21a with respect to the traveling direction axis of the first rail 23 can be changed. It should be noted that a pressure sensor may be provided at the pedal section 21, or an angle sensor, which detects the angle θ, may also be provided at the pedal section 21. An acceleration sensor may be provided at the pedal section 21 to detect the position, speed and acceleration of the pedal section 21. Further, instead of or in combination with the encoder 26, for example, as described in JP 2004-209040 A, the exercise detection section 20 may be configured by using a myopotential sensor. The values of myoelectric potentials generated in a quadriceps femoris muscle, a thigh flexor muscle, and the like, may be detected with an electromyograph, so that the contracted state of muscle, such as the quadriceps femoris muscle or the thigh flexor muscle, is individually acquainted. The signal of each of these various sensors is supplied to a control apparatus 28.

(Load Generation Section)

The exercise apparatus 10 is provided with the load generation section 40 which applies a load to hinder the movement of the pedal section 21. The load of the load generation section 40 can be adjusted with at least one of weight members 44, and, in the present embodiment, the load generation section 40 is in the unloaded state where the weight members 44 is not mounted. The load generation section 40 is provided with a second rail 42, a cage section 41, and a fixing jig 43. The second rail 42 is extended in the Z-axis direction and is fixed to the width W direction end portion of the support body 30, that is, one end of the frame 37. The cage section 41 is movably attached to the second rail 42. One or more weight members 44, each of which is a thin plane block, can be accommodated in the cage section 41. The fixing jig 43 connects the second rail 42 and the support body 30, and can change the position at which the second rail 42 is fixed to the support body 30. It should be noted that, in the embodiment, the second rail 42 is fixed to the width W direction end portion of the support body 30, but in addition, may be fixed to the length L direction end portion of the support body 30. Further, other than the end portion, a cage lifting load generating section corresponding to the second rail 42 may also be provided at any position on the surface of the support body 30 in plan view, for example, near the center of the W×L plane of the support body 30.

(Transmission Wire)

As shown in FIG. 1, the exercise apparatus 10 is provided with the transmission wire 24. In FIG. 1, for convenience, the transmission wire 24 is illustrated by a thick dotted line. The transmission wire 24 is an example of transmission means for transmitting force between the pedal section 21 and the cage section 41. The cage section 41 is displaced on the second rail 42 in conjunction with the movement of the pedal on the first rail 23. The transmission wire 24 is connected to the pedal section 21 and is hung on a pulley (not shown) provided on the side of the first rail 23. One end of the transmission wire 24 is connected to the pedal section 21, and the other end of the transmission wire 24 is connected to the cage section 41. The transmission wire 24 changes the direction via a roller (not shown) at each of position R1 and position R2 in FIG. 1. A cover 45 is provided at the upper portion of the frame 37. It should be noted that, instead of the transmission wire 24, for example, a power transmitting element component, such as a belt or a gear, may also be used.

FIG. 2 shows a state where the exercise apparatus 10 is attached to a bed 200, and the exercising person 2 performs leg press. The exercising person 2, lying on his or her back, places his or her foot 4 on the pedal section 21 of the exercise apparatus 10. The exercising person 2 performs a leg press exercise by bending and stretching the leg 3. The support body 30 is fixed on the bed 200 via an attachment belt 50 which is an example of attachment mean. The attachment mean is, for example, a metal fitting.

Figure 5:
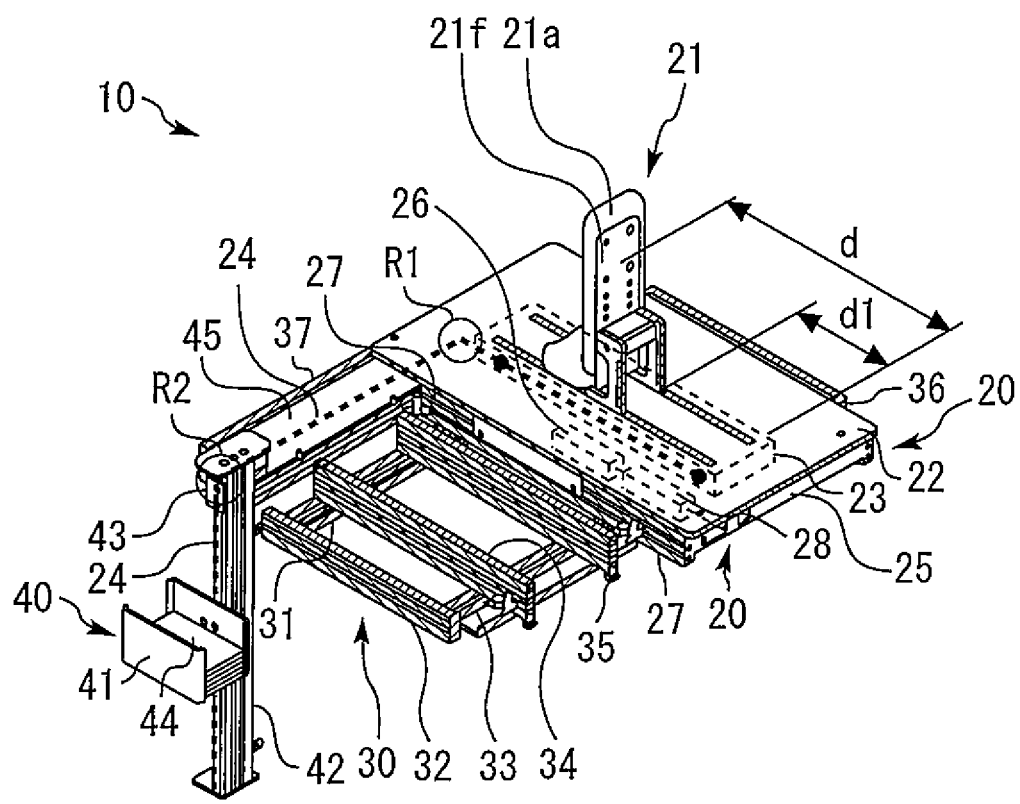
FIG. 5 is a view showing an operation of the exercise apparatus according to the embodiment of the present invention.

FIG. 5 is a view showing the operation of the exercise apparatus 10. FIG. 5 is a view showing the state where the pedal section 21 is advanced on the first rail 23 by d1. When the pedal section 21 is moved by d1, the cage section 41 is moved in conjunction with this movement. Since the weight members 44 is accommodated in the cage section 41, the cage section 41 is urged vertically downward by the action of gravity. This urging force is transmitted as a load by the transmission wire 24, to hinder the movement of the pedal section 21 in the d1 direction.

It should be noted that, in the present embodiment, only the leg press in the unloaded state may be performed. In this case, since it is no necessity to apply a load to the pedal section 21, the exercise apparatus 10 does not need to be provided with the load generation section 40 and the transmission wire 24.

(Control Apparatus)

The control apparatus 28 having therein a processor, a memory, and the like, is mounted in the exercise apparatus 10. The control apparatus 28 is connected to the encoder 26 and can record outputs of the encoder 26 and the other various sensors at fixed time intervals. The exercise apparatus 10 may be connected to an external personal computer via a cable 61, other USB cables, or the like. Thereby, the personal computer can perform information management, such as storing individual electronic data for a plurality of cases. In the case where there are a plurality of exercising persons 2, personal information can also be stored as a database. It should be noted that a database function, or the like, may be mounted in the control apparatus 28.

[Configuration and Operation of Electrical Stimulation Device]

Figure 6:
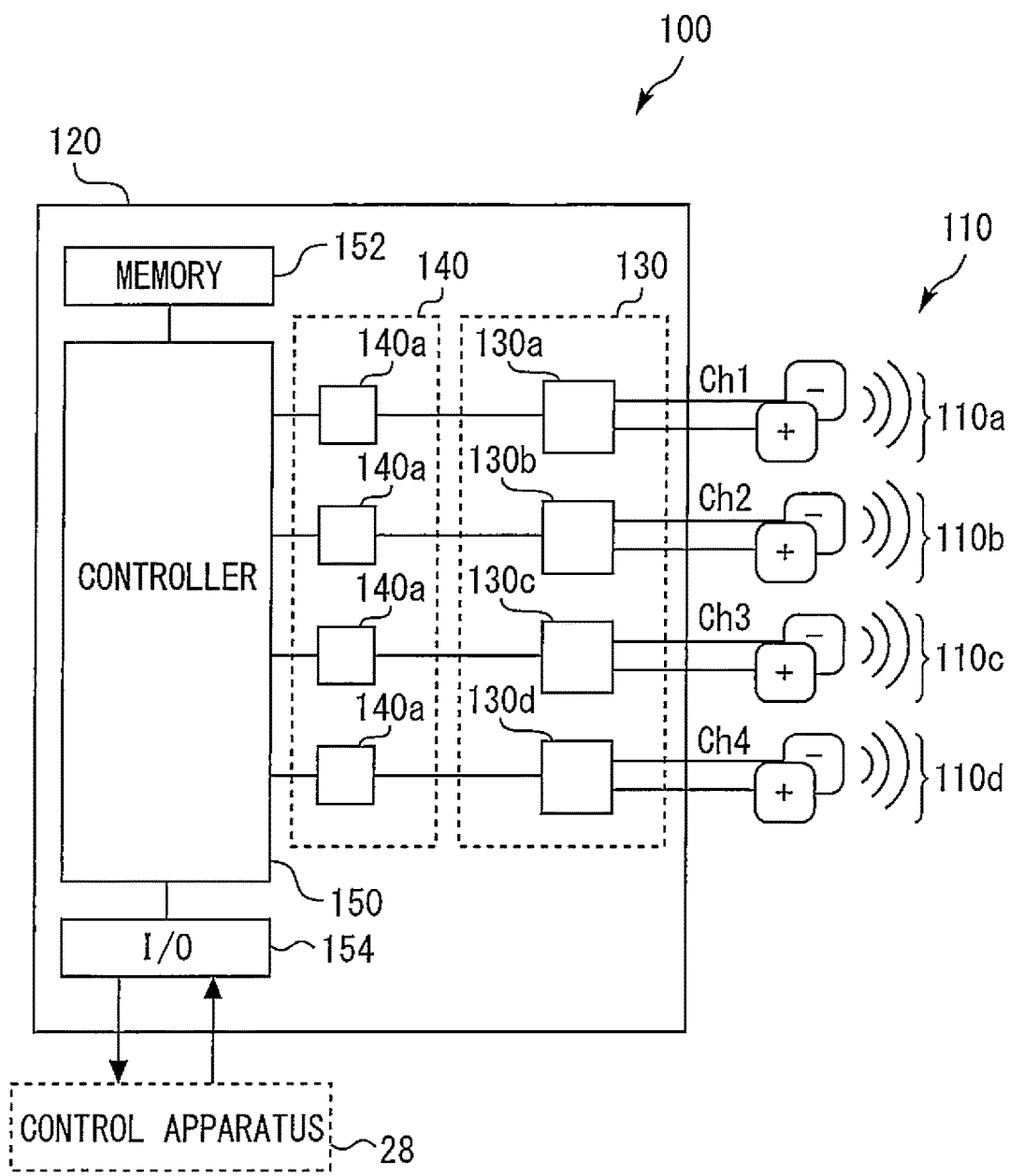
FIG. 6 is a view showing an electrical stimulation device according to the embodiment of the present invention.

FIG. 6 is a view showing the electrical stimulation device 100 according to the embodiment of the present invention. The electrical stimulation device 100 is provided with a plurality of electrode pads 110 each having a plus pole and a minus pole, and an electrical stimulation generation section 120 supplying an electrical stimulation signal to each of the plurality of electrode pads 110. The electrode pads 110 include four electrode pads 110a, 110b, 110c and 110d. Each of the electrode pads 110a to 110d is connected to the electrical stimulation generation section 120 via a wire. As shown in FIG. 6, four channels Ch1 to Ch4 are respectively assigned to the electrode pads 110a to 110d.

The electrical stimulation generation section 120 is provided with: a power circuit 130 which outputs electrical stimulation signals to the electrode pads 110a to 110d; an adjustment circuit 140 which adjusts the output of the power circuit 130; a memory 152 which stores information, such as waveforms of the electrical stimulation signals; an input/output circuit 154 which inputs and outputs data from and to the exterior of the electrical stimulation generation section 120; and a controller 150 which controls the adjustment circuit 140 to change the stimulation intensity according to each of the electrical stimulation signal waveforms read from the memory 152. The power circuit 130 includes power circuit sections 130a to 130d respectively connected to the electrode pad 110a to 110d, so that an individual electrical stimulation can be generated for each of the electrode pads 110a to 110d. The adjustment circuit 140 includes adjustment circuit sections 140a to 140d each of which is connected to each of the power circuit sections 130a to 130d, and each of which can adjust electrical stimulation for each of the electrode pads 110a to 110d. Specifically, the adjustment of electrical stimulation includes adjustment of the strength of stimulation, that is, the intensity of stimulation. The adjustment of intensity of stimulation may be performed on the basis of various known electrical stimulation techniques, but specifically, may be performed by adjusting voltage values or current values respectively applied to the electrode pads 110a to 110d. For example, as disclosed in JP 2008-67917 A, AC voltages and pulse voltages may be used, or AC currents and pulse currents may also be used. The preferred ranges of frequency, period, duty, and the like, of the voltage values or the current values may be suitably selected.

The memory 152 stores control programs, such as waveforms of the electrical stimulation signals, and the like, described below. Specifically, the memory 152 stores information on first stimulation patterns A1 to A4, information on second stimulation patterns B1 to B4, and information required for generating a plurality of waveforms respectively included the stimulation patterns. The electrical stimulation generation section 120 respectively supplies electrical stimulation signals of Ch1 and Ch2 to the electrode pads 110a and 110b according to the first stimulation patterns A1 to A4, and respectively supplies electrical stimulation signals of Ch3 and Ch4 to the electrode pads 110c and 110d according to the second stimulation patterns B1 to B4. The first stimulation pattern A1 to A4 are set beforehand so that the electrical stimulation signal of Ch1 is supplied to the electrode pad 110a, and the electrical stimulation signal of Ch2 is supplied to the electrode pad 110b. The second stimulation patterns B1 to B4 are set beforehand such that the electrical stimulation signal of Ch3 is supplied to the electrode pad 110c, and the electrical stimulation signal of Ch4 is supplied to the electrode pad 110d.

In the present embodiment, the electrical stimulation device 100 is separately provided outside the exercise apparatus 10, but the present invention is not limited to this. The electrical stimulation device 100 may be stored in the exercise apparatus 10, that is, in the case 25, so that the electrode pad 110a to the electrode pad 110d can be are extracted to the outside of the exercise apparatus 10. Further, in the present embodiment, it is described that the control apparatus 28 and the electrical stimulation device 100 are formed as different hardware devices. However, this configuration is an example, and the present invention is not limited to this. For example, a processor, a memory, and the like, may be commonly used between the control apparatus 28 and the electrical stimulation device 100.

Figure 7:
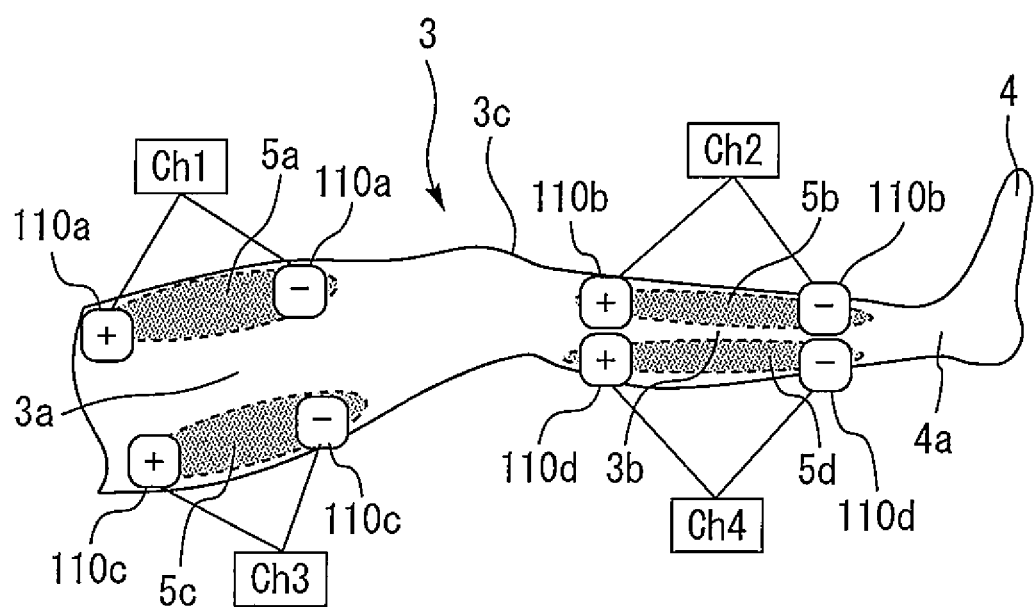
FIG. 7 is a schematic view explaining an electrical stimulation method according to the embodiment of the present invention.

Muscle Strength Training Using the Electrical Stimulation Method According to the Embodiment. Each of FIG. 7 to FIG. 12 is a schematic view for explaining muscle strength training using the electrical stimulation method according to the embodiment of the present invention. FIG. 7 shows the leg 3 of the exercising person 2. The leg 3 is provided with a thigh portion 3a, a lower thigh portion 3b, a knee 3c, the, 4, and an ankle 4a. The stimulation of Ch1 is applied to a quadriceps femoris muscle 5a by the electrode pad 110a, and thereby stimulates the quadriceps femoris muscle 5a to extend the knee 3c. The stimulation of Ch2 is applied to a tibialis anterior muscle 5b by the electrode pad 110b and thereby stimulates the tibialis anterior muscle 5b to dorsiflex the ankle 4a. The stimulation of Ch3 is applied to a biceps femoris muscle 5c by the electrode pad 110c and thereby stimulates the biceps femoris muscle 5c to bend the knee 3c. The stimulation of Ch4 is applied to a gastrocnemius muscle 5d by the electrode pad 110d and thereby stimulates the gastrocnemius muscles 5d to plantar flex the ankle 4a. The exercise is promoted by bending the leg 3, and in conjunction with the bending, the stimulation of Ch4 is supplied to a calf (gastrocnemius muscle) to thereby plantar flex the leg 3. After the bending, the exercise is promoted by extending the leg 3, and in conjunction with the extending, the stimulation of Ch2 is supplied to a shank (tibialis anterior muscle) to thereby dorsiflex the leg 3. In the electrical stimulation method according to the present embodiment, the application of the electrical stimulations of Ch3 and Ch4 for bending and plantar flexion, and the electrical stimulations of Ch1 and Ch2 for extension and dorsiflexion are alternately performed. It should be noted that which of the application of the electrical stimulations of Ch3 and Ch4 and the application of the electrical stimulations of Ch1 and Ch2 is performed first may be arbitrarily set according to which of a state S1 and a state S2 is set as an initial state.

Figure 8:
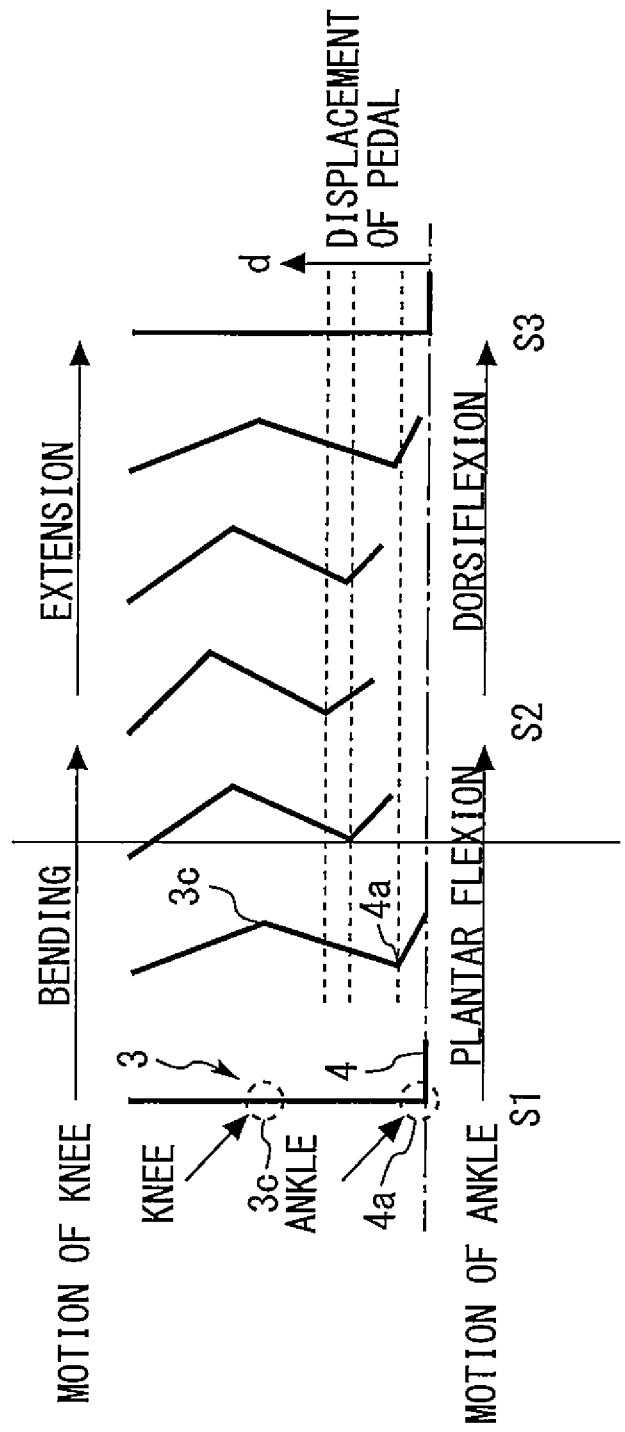
FIG. 8 is a schematic view explaining the electrical stimulation method according to the embodiment of the present invention.

FIG. 8 is a view for explaining the motion of the knee 3c and the ankle 4a when the stepping is performed on the spot. The state S1 is the upright state where the leg 3 is stretched. The knee is gradually bent from the state S1, and thereby the ankle is gradually plantar flexed to be in the state S2. The state S2 is the state where the knee is moved to the peak position during stepping. The knee 3c is gradually extended from the state S2, and thereby the ankle 4a is gradually dorsiflexed to be in the state S3. The state S3 is the state where the leg 3 is fully stretched to again return to the upright state.

Figure 9:
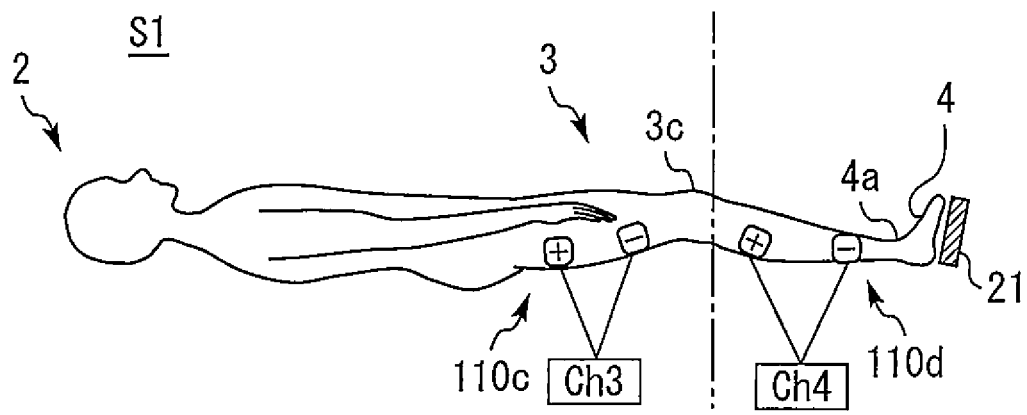
FIG. 9 is a schematic view explaining the electrical stimulation method according to the embodiment of the present invention.
Figure 10:
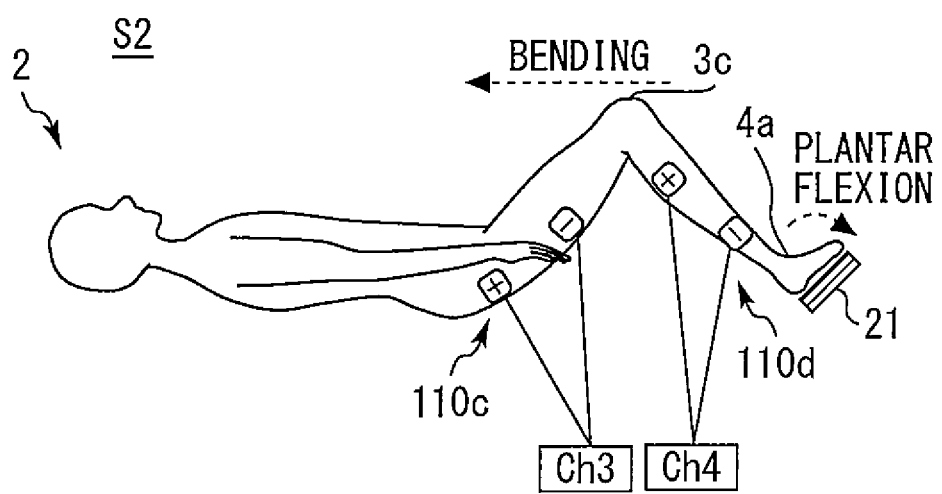
FIG. 10 is a schematic view explaining the electrical stimulation method according to the embodiment of the present invention.
Figure 11:
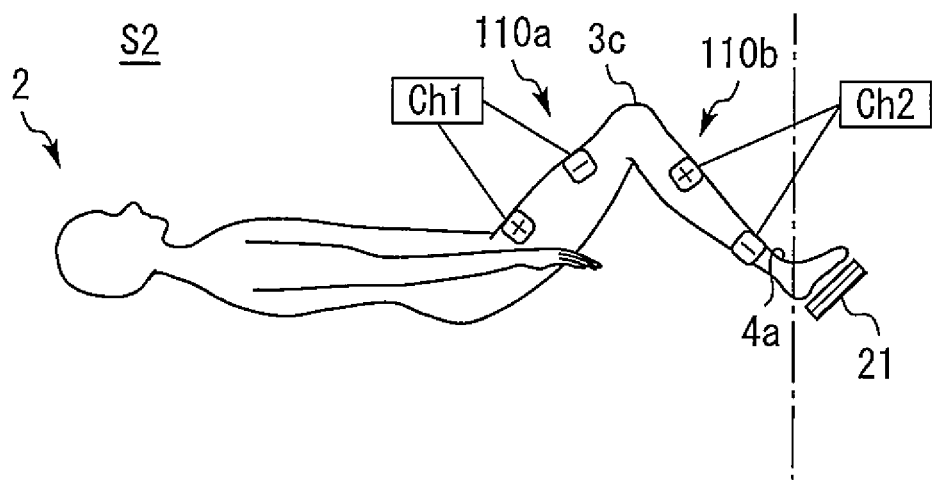
FIG. 11 is a schematic view explaining the electrical stimulation method according to the embodiment of the present invention.
Figure 12:
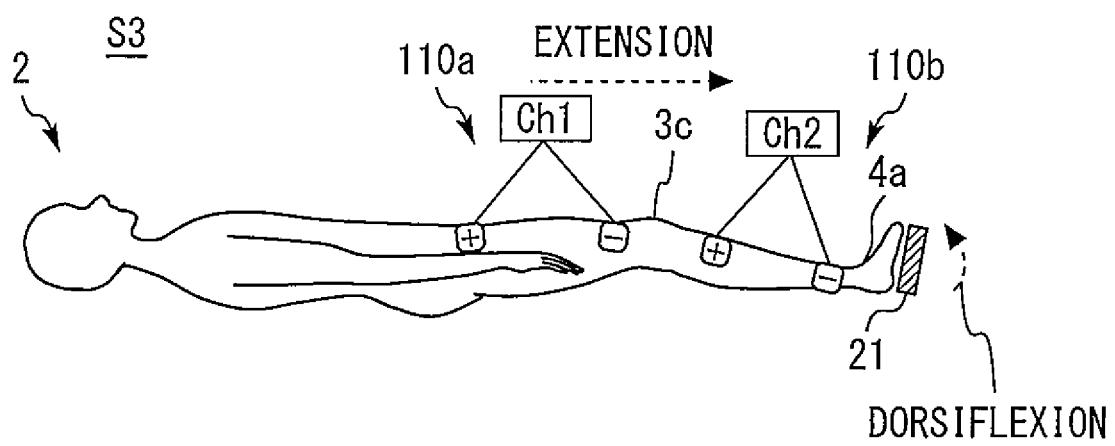
FIG. 12 is a schematic view explaining the electrical stimulation method according to the embodiment of the present invention.

FIG. 9 to FIG. 12 show the electrical stimulation method for realizing the stepping motion of FIG. 8. FIG. 9 shows the state S1. The knee 3c is bent by supplying an electrical stimulation signal of Ch3 to the electrode pad 110c, and the ankle 4a is plantar flexed by supplying an electrical stimulation signal of Ch4 to the electrode pad 110d. Thereby, the leg 3 is in the state S2 of FIG. 10. Then, in the state S2 of FIG. 11, the knee 3c is extended by supplying an electrical stimulation signal of Ch1 to the electrode pad 110a, and the ankle 4a is dorsiflexed by supplying an electrical stimulation signal of Ch2 to the electrode pad 110b. Thereby, the leg 3 is in the state S3 of FIG. 12. The motions in the states S1, S2, S3, S1, S2, S3 . . . are repeatedly performed by respectively supplying the electrical stimulation signals of Ch1 to Ch4.

Waveforms of Electrical Stimulation Signals According to the Embodiment. FIG. 13 to FIG. 16 are waveform charts of the electrical stimulation signals generated by the electrical stimulation device 100 according to the embodiment of the present invention. FIG. 13 to FIG. 16 shows first stimulation patterns A1 to A4 and second stimulation patterns B1 to B4. In each of the channels Ch1 to Ch4, the horizontal axis represents time, and the vertical axis represents stimulation intensity. In each of FIG. 14 to FIG. 16, the walking states are schematically illustrated above the waveform charts on the paper surface. According to the waveforms shown in FIG. 13 to FIG. 16, the training apparatus 1 makes the exercising person 2 perform muscle strength training by using the electrical stimulation signals of Ch1 to Ch4. As shown in FIG. 13 to FIG. 16, the stimulation intensity of each of the Ch1 to Ch4 is changed according to each of waveforms 161 to 175. The waveform of Ch2 is increased and decreased in conjunction with the waveform of Ch1, and the waveform of Ch4 is increased and decreased in conjunction with the waveform of Ch3.

As shown in FIG. 13 to FIG. 16, the electrical stimulation device 100 alternately performs electrical stimulations of the first stimulation patterns A1 to A4, and electrical stimulations of the second stimulation patterns B1 to B4. Thereby, the electrical stimulation device 100 can alternately perform the electrical stimulation by Ch1 and Ch2, and the electrical stimulation by Ch3 and Ch4. The phrase "alternately perform electrical stimulations" here is not limited to the state where the stimulation patterns shown in FIG. 13 to FIG. 16 are respectively repeated. For example, after two or more stimulation patterns arbitrarily selected from the first stimulation patterns A1 to A4 are continued, at least one of the second stimulation patterns B1 to B4 may be applied. Alternatively, after two or more stimulation patterns arbitrarily selected from the second stimulation patterns B1 to B4 are continued, at least one of the first stimulation patterns A1 to A4 may be applied. These stimulation patterns may also be repeated continuously or with predetermined stop intervals.

It is preferred that the electrical stimulations of Ch1 and Ch2, and the electrical stimulations of Ch3 and Ch4 are not simultaneously applied. It is preferred that, according to the first stimulation patterns A1 to A4 and the second stimulation patterns B1 to B4, the electrical stimulations of Ch1 and Ch2 and the electrical stimulations of Ch3 and Ch4 are mutually exclusively applied. When a rest time is provided between the application of the electrical stimulations by the first stimulation patterns A1 to A4, and the application of the electrical stimulations by the second stimulation patterns B1 to B4, the electrical stimulation application can be exclusively performed to the exercising person 2 while reducing a load to the exercising person 2. However, the present invention is not limited to these methods of applying the electrical stimulations. Here, the method of "alternately performing application of electrical stimulations" includes a method in which, while the set of electrical stimulations of the first stimulation patterns A1 to A4, and the set of electrical stimulations of the second stimulation patterns B1 to B4, are alternately generated with a time interval, the electrical stimulations of the sets partially overlap with each other.

Figure 13:
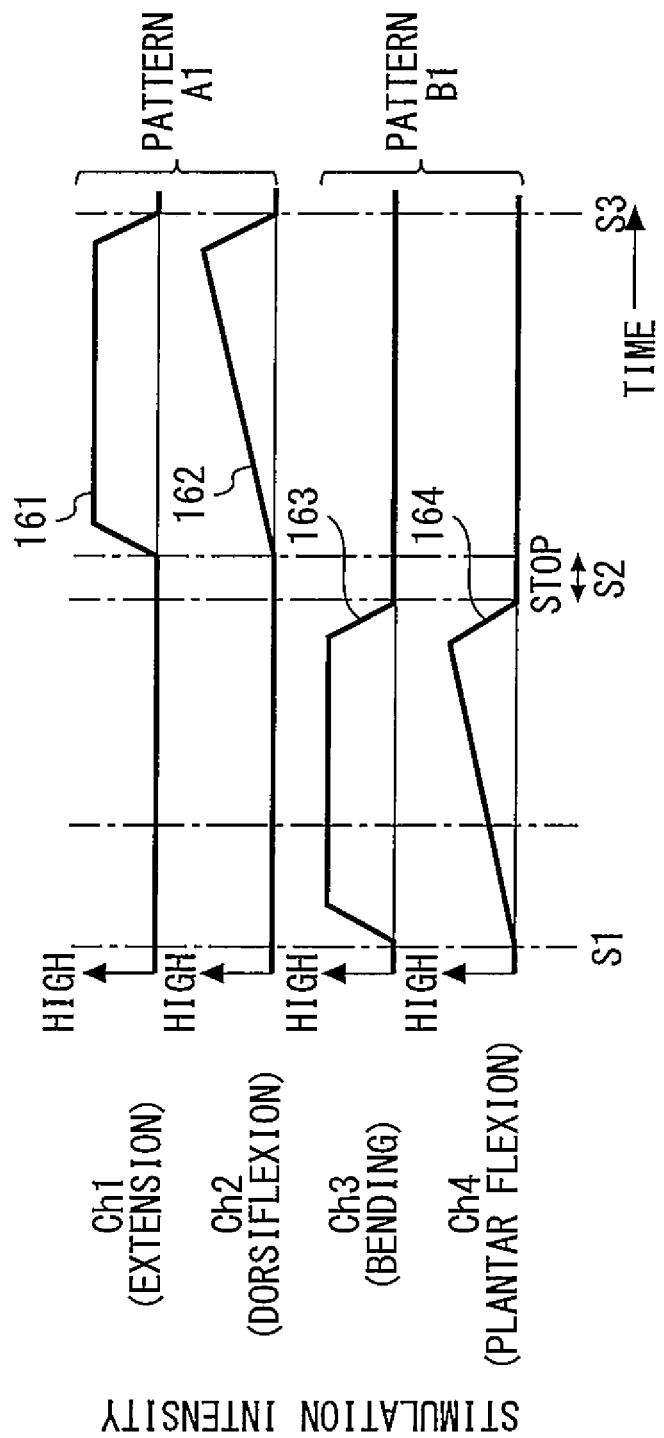
FIG. 13 shows waveform charts of electrical stimulation signals according to the embodiment of the present invention.

FIG. 13 shows waveforms of the electrical stimulation signals for realizing the stepping motion shown in FIG. 9 to FIG. 12. In an example shown in FIG. 13, each of the waveforms 161 and 163 of Ch1 and Ch3 is a trapezoidal waveform, and each of the waveforms 162 and 164 of Ch2 and Ch4 is a triangular waveform. Each of the triangular waveforms of Ch2 and Ch4 has a shape in which the increasing slope is steeper than the decreasing slope, and in which the increasing period is longer than the decreasing period. For the transition from the state S1 to the state S2, each of the electrical stimulations of Ch3 and Ch4 is turned on. Upon reaching the state S2, each of the electrical stimulations of Ch3 and Ch4 is turned off, and then, each of the electrical stimulations of Ch1 and Ch2 is turned on. Upon reaching the state S3 from the state S2, each of the electrical stimulations of Ch1 and Ch2 is turned off, so that one reciprocating motion of leg press is completed.

Figure 14:
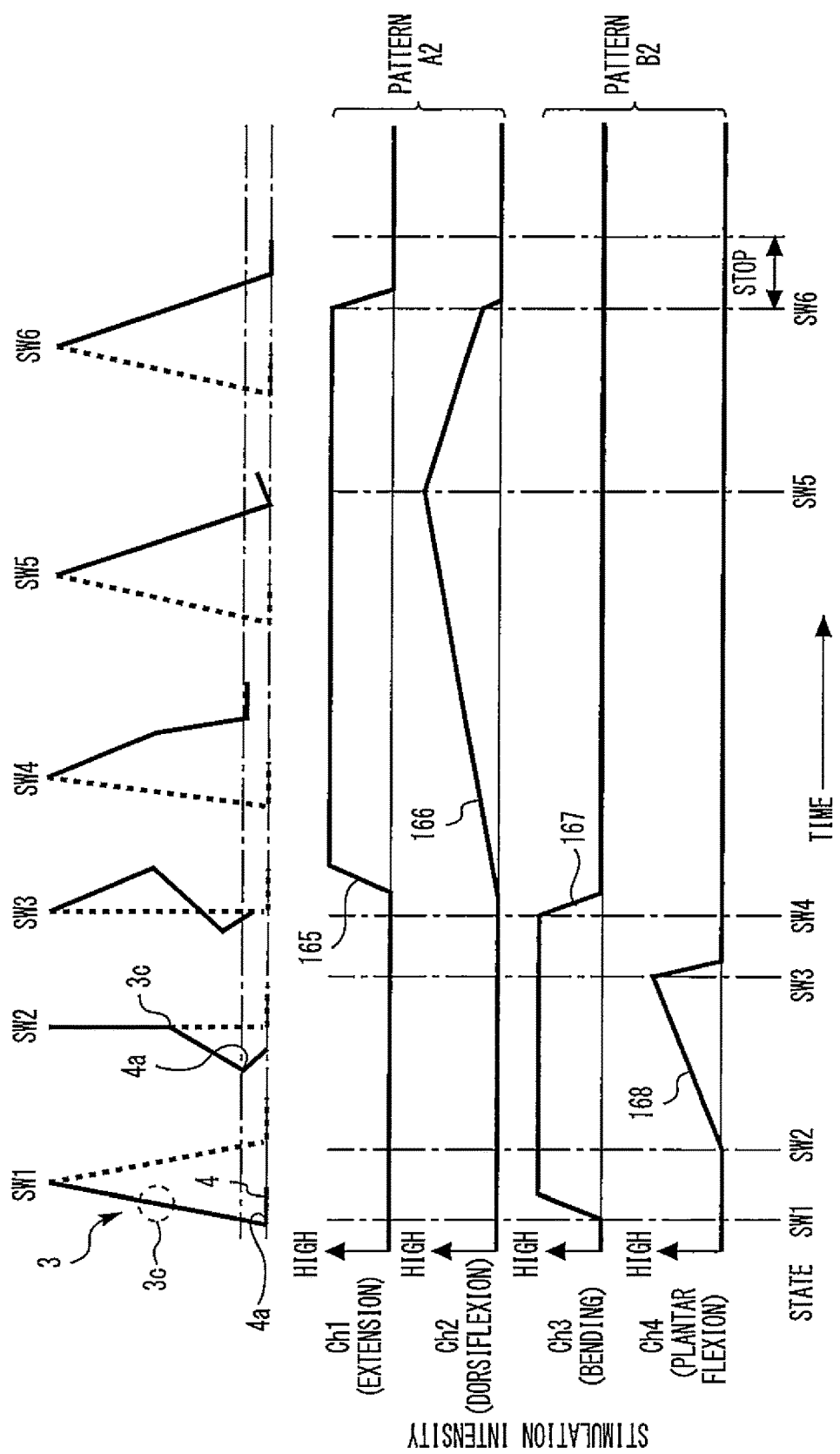
FIG. 14 shows waveform charts of the electrical stimulation signals according to the embodiment of the present invention.
Figure 15:
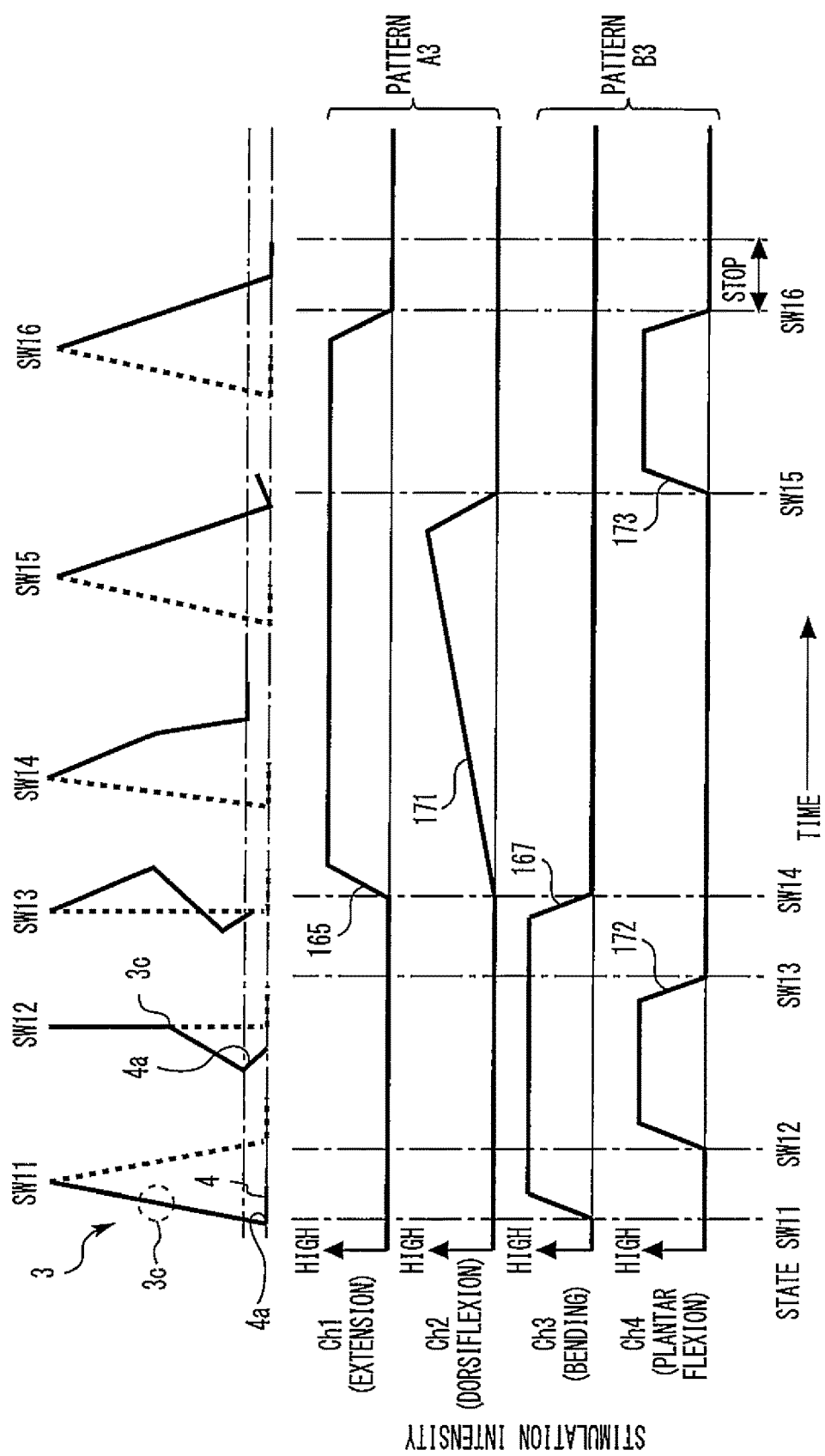
FIG. 15 shows waveform charts of the electrical stimulation signals according to the embodiment of the present invention.
Figure 16:
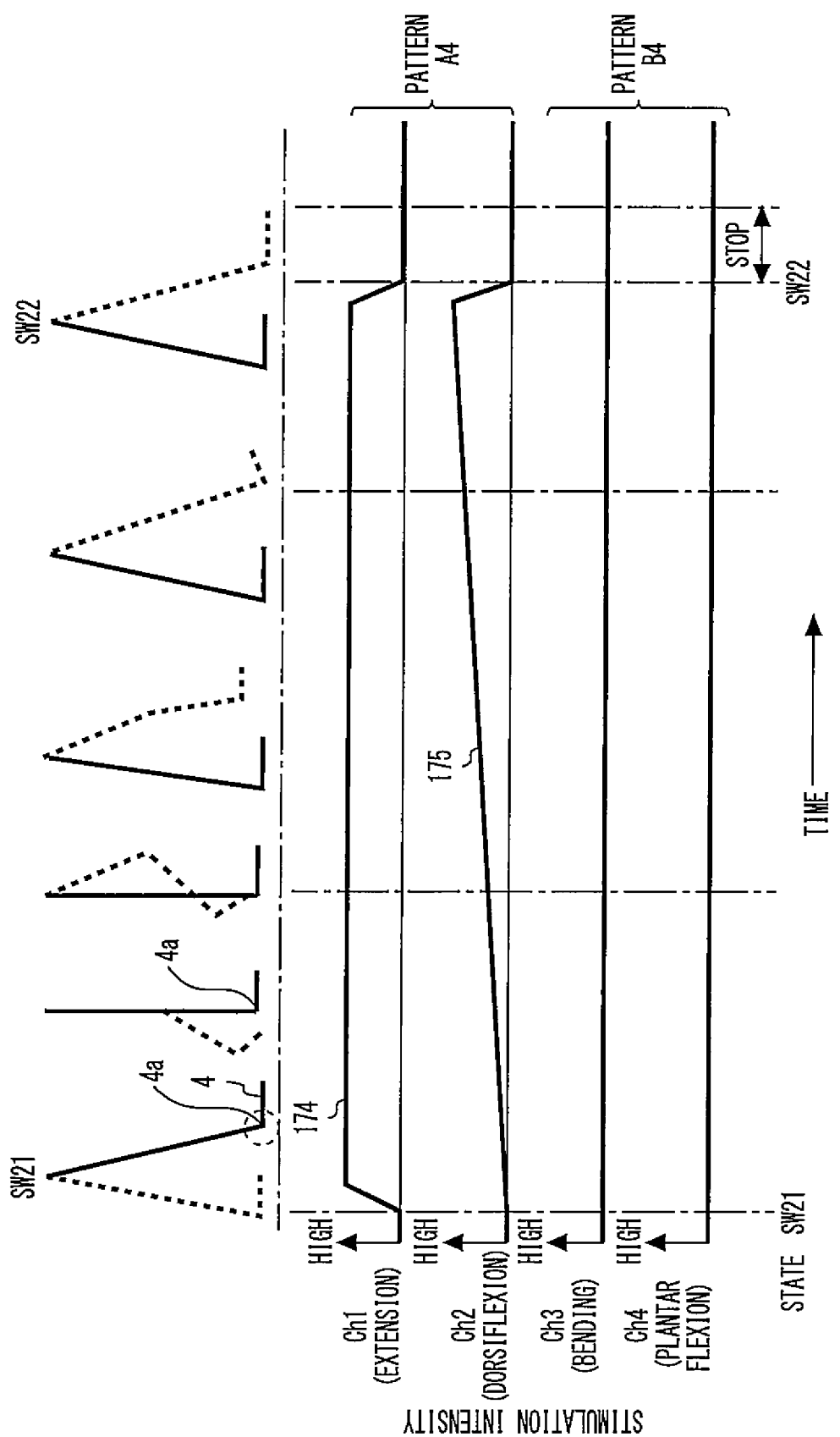
FIG. 16 shows waveform charts of the electrical stimulation signals according to the embodiment of the present invention.

Each of FIG. 14 to FIG. 16 shows waveforms of electrical stimulation signals for realizing motions at the time of walking. FIG. 14 shows waveforms used at the time of muscle strength training in which the leg is moved forward. In FIG. 14, electrical stimulation signals of waveforms 165 to 168 are respectively supplied to Ch1 to Ch4, and thereby, the state of the leg 3 is transitioned to states SW1 to SW6. The state SW1 is an initial state. The state SW1 is the state of the leg 3 which starts to bend for moving forward. The state SW1 corresponds to the timing when the waveform 167 of Ch3 starts to increase. The state SW2 is the state of the leg 3 which starts plantar flexion for kicking the ground surface. The state SW2 corresponds to the timing when the waveform 167 of Ch3 is held at the peak value and when the waveform 168 of Ch4 starts to increase. The state SW3 is the state of the leg 3 which ends the plantar flexion since the foot 4 leaves the ground by kicks the ground. The state SW3 corresponds to the timing when the waveform 168 of Ch4 reaches a peak value and starts to decrease. The state SW4 is the state of the leg 3 which ends bending when bending to reach a predetermined position and starts extension and dorsiflexion for moving forward. The state SW4 corresponds to the timing when the waveform 167 of Ch3 starts to decrease. In the section between the state SW4 and the state SW5, first, the waveform 167 of Ch3 falls down to zero. When the waveform 167 of the Ch3 decreases to zero, the waveform 165 of Ch1 and the waveform 166 of Ch2 start to increase. The state SW5 is the state of the leg 3 which gradually reducing the output for dorsiflexion when extending to reach the ground surface. The state SW5 corresponds to the timing when the waveform 166 of Ch2 changes from increase to decrease. The state SW6 is the state of the leg 3 which ends extension and dorsiflexion since the back of the foot 4 is attached to the ground surface. The state SW6 corresponds to the exit status. From the state SW6, the exercising person 2 is made to rest during an "exercise stop period" set beforehand. Thereafter, the motions of the state SW1 and the states after the state SW1 described above are repeatedly performed. It is preferred that each of the states SW1 to SW6, and each of the positions of the pedal section 21 are stored in the control apparatus 28, and that the states SW1 to SW6 are detected on the basis of the output of the encoder 26. The angle θ of the pedal section 21 may be detected by an angle sensor, or the like, to more accurately detect the motion state of the pedal section 21.

FIG. 15 shows a modification of the waveforms of the electrical stimulation signals of FIG. 14. FIG. 15 is different from FIG. 14 in that the waveform 171 of Ch2 is a triangular wave and Ch2 falls downs during the peak of Ch1, and in that the waveform 172 of Ch4 is a trapezoidal wave, and the waveform 173 of Ch4 exists in the latter part of Ch1, so that the on section of Ch1 overlap with the on section of Ch4. FIG. 16 shows the waveforms for producing a walking motion after FIG. 14 and FIG. 15. The walking motion is connected from the state SW6 or SW16 to the state SW21.

The first stimulation pattern A4 and the second stimulation pattern B4 which are shown in FIG. 16 are configured only such that the waveform 174 of Ch1 is a trapezoidal wave, and such that the waveform 175 of Ch2 is a triangular wave. The waveform of Ch3 and Ch4 are kept to be off. The section length between the state SW21 to the state SW22 is the same as the section length between the state SW1 (or SW11) and the state SW6 (or SW16). The walking motion is connected from the state SW22 to the state SW1 or SW11.

The waveforms of an electrical stimulation signals can be variously set according to objective exercise. An example about the setting, there will be described an example in which the magnitude of an electrical stimulation signal is proportional to the intensity of the electrical stimulation. The strength of stimulation of each of Ch1 to Ch4 is correlated with the amount of displacement of the leg 3, that is, each of the amount of extension, the amount of dorsiflexion, the amount of bending, and the amount of plantar flexion. Further, the rate of change of an electrical stimulation signal is proportional to the "rate of change of intensity of stimulation". When the rate of change of the waveform is large, a stimulation moving the leg 3 quickly is generated, while, when the rate of change of the waveform is small, a stimulation moving the leg 3 gradually and slowly is generated. Therefore, as shown in FIG. 14 and FIG. 15, the stimulation supply period of each of the first stimulation patterns A2 and A3 is set longer than the stimulation supply period of each of the second stimulation patterns B2 and B3. Thereby, it is possible to perform muscle strength training close to an actual walking motion.

Here, the waveforms 161, 163, 165, 167 and 174 belonging to Ch1 or Ch3 are referred to as a "first waveform group", and the waveforms 162, 164, 166, 168, 171, 172, 173, and 175 belonging to Ch2 or Ch4 are referred to as a "second waveform group". The first waveform group includes the waveforms of the electrical stimulation signals which perform extension and bending of the knee 3c. The second waveform group includes the waveforms of the electrical stimulation signals which perform dorsiflexion and plantar flexion of the ankle 4a. Therefore, one or more of following relationships may be preferably applied. As shown in FIG. 14 to FIG. 16, the waveforms of the first waveform group and the waveforms of the second waveform group may be increased so that, after each of the waveforms of the first waveform group reaches a peak, each of the waveforms of the second waveform group reaches a peak, The on sections of the waveforms of the first waveform group may be at least partly overlap with the on sections of the waveforms of the second waveform group. The waveforms of the second waveform group may be increased to reach the peak values in the sections in which the waveform of the first waveform group are held at the peak value. The waveforms of the second waveform group may start to decrease in the sections in which the waveforms of the first waveform group are held at the peak value. The section showing the peak value of the waveforms of the second waveform group may be shorter than the section showing the peak value of the waveforms of the first waveform group. The rising inclination of the waveform of the second waveform group may be smaller than the falling inclination of the waveform of the second waveform group. As in the waveform 166, the waveform of the second waveform group includes a first reduction section in which the value of the waveform is reduced at a first inclination, and a second reduction section in which the value of the waveform is reduced at a second inclination higher than the first inclination.

Further, the peak value (that is, amplitude) may be made different among the plurality of the waveforms 161 to 174. Thereby, the amount of extension, the amount of dorsiflexion, the amount of bending, and the amount of plantar flexion may be adjusted respectively. The relationship between the waveforms of "two Chs" of Ch1 to Ch4 may be set as follows. At least one of the rate of change at the time of waveform increase, and the rate of change at the time of waveform decrease may be different between the waveforms of two Chs. The waveform decrease or the waveform decrease may be changed stepwise or continuously. At least one of the length of the section of waveform increase and the length of the section of waveform decrease may be different between the waveforms of two Chs. At least one of the time when the waveform increase starts, and the time when the waveform decrease starts may be different between the waveforms of two Chs. At least one of the time when the waveform increase ends, and the time when the waveform decrease ends may be different between the waveforms of two Chs. Specifically, the "two Chs" may be a pair of Ch1 and Ch2, a pair of Ch3 and Ch4, a pair of Ch1 and Ch3, or a pair of Ch2 and Ch4.

Further, among the first stimulation patterns A1 to A4, and among the second stimulation patterns B1 to B4, the on sections of a plurality of the waveforms belonging to the same stimulation pattern may overlap with each other or may not overlap with each other. For example, in FIG. 14, the on sections of the waveforms 167 and 168 belonging to the second stimulation pattern B2 overlap with each other. However, the on sections of the waveforms 167 and 168 may not be made to overlap with each other in such a manner that the waveform 167 is made to fall down earlier than when the waveform 168 starts to increase. Further, it is preferred that the stimulation intensity of each of the electrode pads 110a to 110d can be independently set. Since motions of persons are different from person to person, it is preferred that all of the increasing waveform, the constant waveform, and the decreasing waveform can be suitably adjusted by the user. In the case where a person feels a slight pain in the knee joint, or in the case where, since the waveform increase is rapid, a person feels pain, the slope of the waveform inclination may be reduced. It is preferred that, when the waveform is held constant, the length of the constant section and the constant intensity can be suitably adjusted. The slope of the decreasing waveform may be reduced. Similarly, it is preferred that the peak value of the waveform, that is, the maximum value of the intensity of stimulation to be applied can also be adjusted. As a specific example of the adjustment method, in the case where there are a plurality of users, an identification number (ID) may be assigned to each of the users so that a group of the above-described parameters are set for each of the users. The group of the parameters for each of the users may be switched.

The extension and bending of the knee 3c can be performed with the stimulations of the electrode pads 110a and 110c, while the dorsiflexion and plantar flexion of the ankle 4a can be performed with the stimulations of the electrode pads 110b and 110d. The plantar flexion of the ankle 4a is performed in conjunction with the bending of the knee 3c, while the dorsiflexion of the ankle 4a is performed in conjunction with the extension of the knee 3c. In this way, a set of the bending and the plantar flexion, and a set of the extension and the dorsiflexion are alternately performed, to thereby realize motion, such as bending and extension, stepping, or walking. As shown in FIGS. 13 to 16, the group of the first stimulation patterns A1 to A4, and the group of the second stimulation patterns B1 to B4 are alternately supplied, and thereby, electrical stimulations inducing the motion, such as bending and extension, stepping, or walking, can be accurately applied to the leg 3. Thereby, more accurate and practical muscle strength training can be performed. The present embodiment is based on the muscle strength training by the leg press. However, as a preferred application target, the present invention can be applied to stepping and walking training, in order to increase muscular power to perform motions, such as stand up from the spot, sitting, squatting, and standing on the spot. The present invention is not limited to the muscle strength training for walking, but can be applied to muscle strength training for running.

Specific Control of Training Apparatus According to the Embodiment.

Each of FIG. 17 to FIG. 20 is a control flow chart of the training apparatus 1 according to the embodiment of the present invention. The process steps having the same or similar functions are denoted by the same reference characters, and the description thereof is omitted. This control may be carry out by control means provided in the training apparatus 1. The process of each of the steps may be suitably shared by the control apparatus 28 and the controller 150. It should be noted that, as shown by the waveform charts described above, in the present embodiment, the rising edge rises at a predetermined increase rate when the stimulation is turned on, and the falling edge falls at a predetermined decrease rate when the stimulation is turned off. Thereby, a rapid stimulation change is suppressed. However, the present invention is not limited to this, and at least one of the rising and falling of the waveform may be instantaneously changed.

Figure 17:
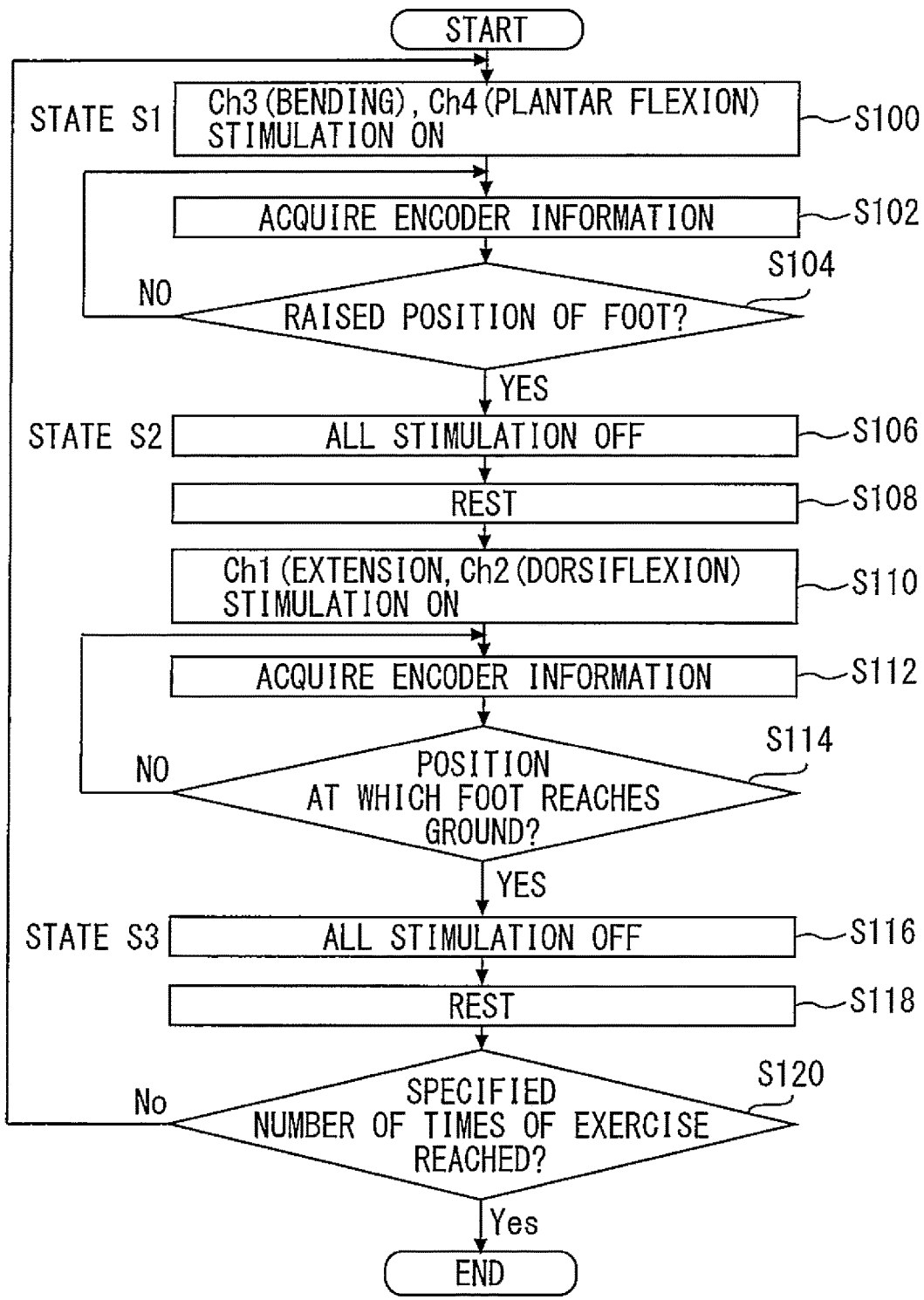
FIG. 17 is a control flow chart of the training apparatus of the embodiment of the present invention.

FIG. 17 shows the control which realizes a stepping motion. In FIG. 17, first, in step S100 in state S1, the stimulations of Ch3 and Ch4 are turned on. Thereby, the electrical stimulation signals of Ch3 and Ch4 shown in FIG. 13 are outputted to the electrode pads 110c and 110d. Next, in step S102, the control apparatus 28 acquires the output of the encoder 26, to acquire the position information on the pedal section 21. Next, in step S104, determination processing is performed. When the pedal section 21 has reached the position set beforehand, the process proceeds to step S106, and when the pedal section 21 has not reached the position set beforehand, the process returns to step S102. The "position set beforehand" is the position corresponding to the position of the raised foot 4 in the state S2. In step S106 in state 52, all of the stimulations of Ch1 to Ch4 are turned off. Next, in step S108, time is counted until the elapsed time reaches the rest time set beforehand. When the rest time in step S108 is ended, then, in step S110, the stimulations of Ch1 and Ch2 are turned on. Next, in step S112, the control apparatus 28 acquires the output of the encoder 26, and in step S114, the control apparatus 28 determines whether or not the pedal section 21 has reached the original position. When the pedal section 21 has reached the original position, the foot 4 is in the state of touching the ground surface in state S3. At the time when the condition of step S114 is established, the process proceeds to step S116 to turn off all of the stimulations, and in step S118, time is counted until the elapsed time reaches the rest time set beforehand. Thereafter, in step S120, the count value of the integrated number of times of exercise is incremented to determine whether or not the integrated number of times of exercise has reached the specified number of times of exercise. Until the integrated number of times of exercise reaches the specified number of times of exercise, the process of steps S100 to S120 are repeated. When the integrated number of times of specified has reached the specified number of times of specified, the routine of FIG. 17 is ended.

Figure 18:
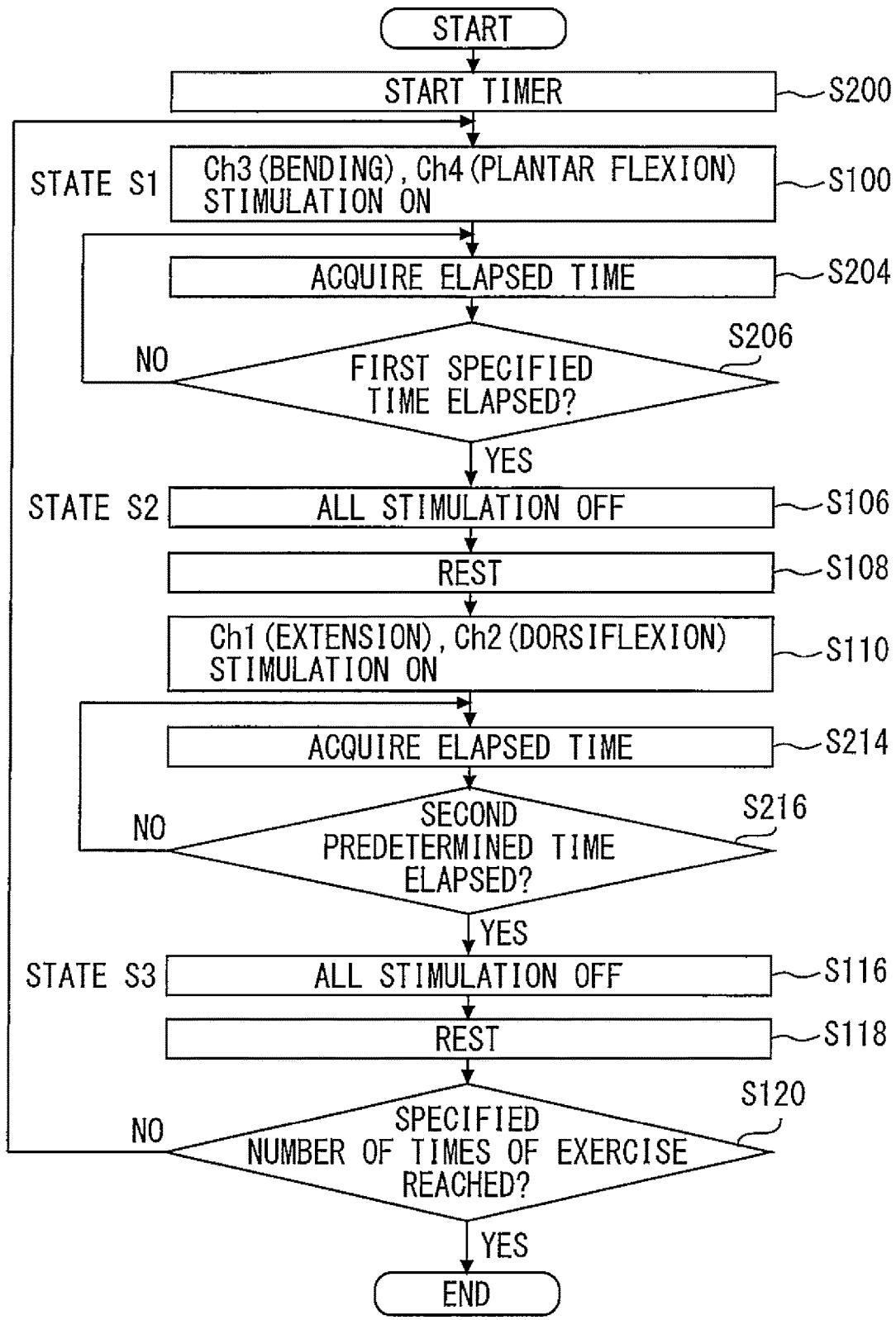
FIG. 18 is a control flow chart of the training apparatus of the embodiment of the present invention.

FIG. 18 shows a modification of the routine of FIG. 17. In the routine of FIG. 18, turning on and off of Ch1 to Ch4 are changed on the basis of the time measurement value. In the routine of FIG. 18, first, time measurement by a timer is started in step S200. Next, similarly to FIG. 17, the process of step S100 is performed. Next, in step S204, elapsed time is measured after execution of the process in step S100. Next, in step S206, it is determined whether or not the elapsed time has reached a first predetermined time set beforehand. The "first predetermined time" is the time from when stimulation is turned on in step S100 to the state S2 where the foot 4 is raised. The first predetermined time may be set to be equal to the on period of Ch3 of FIG. 13. When, in step S206, it is determined that the elapsed time has reached the time set beforehand, the process proceeds to step S106, S108 and S110. Then, the elapsed time is acquired in step S214, and in step S216, it is determined whether or not the elapsed time has reached a second predetermined time set beforehand. The "second predetermined time" is the time from when the stimulation is turned on in step S110 to the time when the pedal section 21 is estimated to have returns the initial position, and may be set to be equal to the on period of Ch1 in FIG. 13. When the condition of step S216 is established, similarly to the routine in FIG. 17, turning off of all of the stimulations in step S116, rest in step S118, and determination of the number of times of exercise in step S120 are performed. When the integrated number of times of exercise has reached the specified number of times of exercise, the routine is ended.

Figure 19:
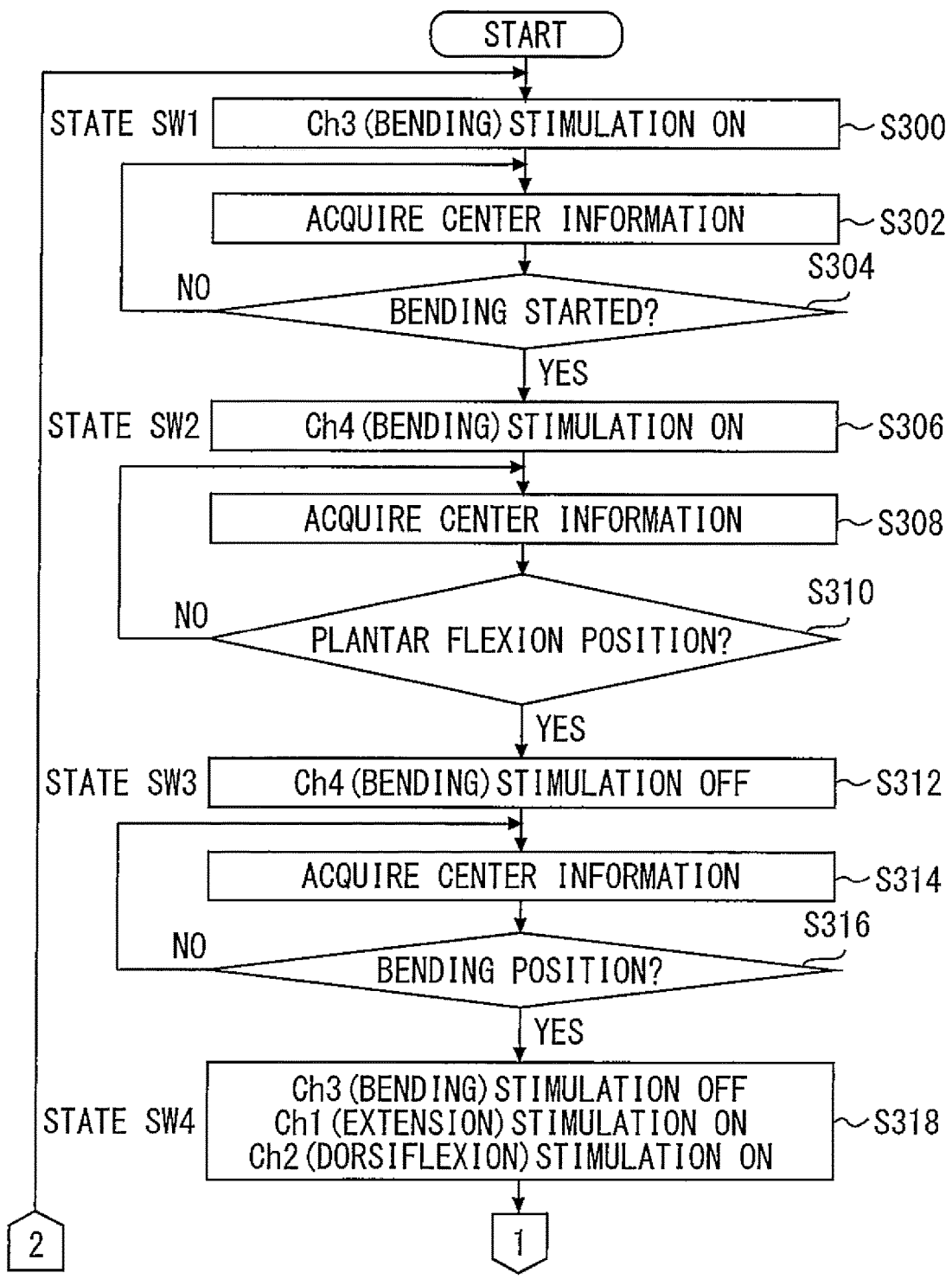
FIG. 19 is a control flow chart of the training apparatus of the embodiment of the present invention.
Figure 20:
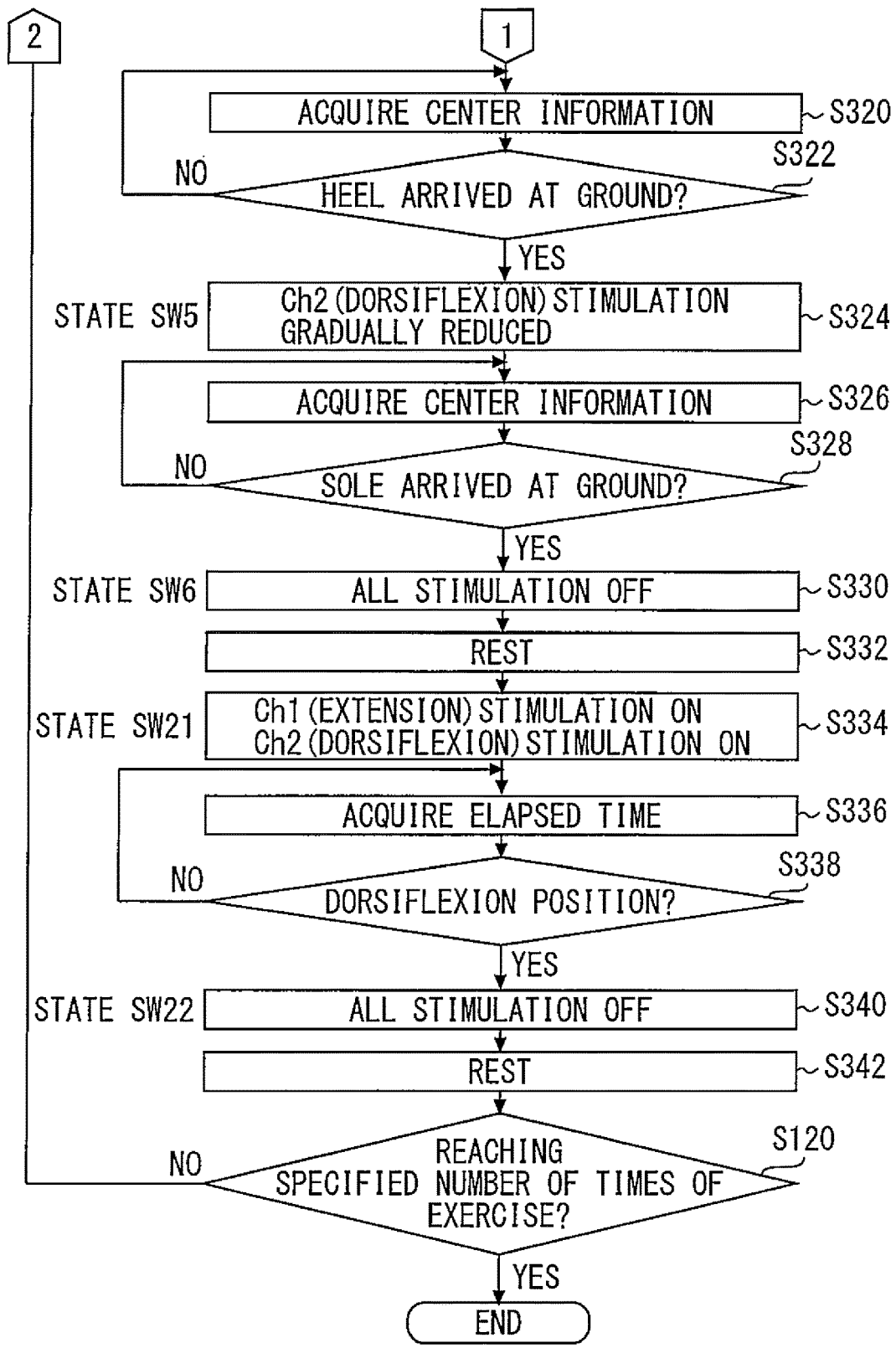
FIG. 20 is a control flow chart of the training apparatus of the embodiment of the present invention.

FIG. 19 and FIG. 20 are control flow charts in which stimulation signals are applied according to the waveform charts showing in FIG. 14 and FIG. 16. In the routine of FIG. 19, first, in step S300, when the leg 3 is in the state SW1, the stimulation of Ch3 is turned on. Next, in step S302, sensor information acquisition processing for acquiring the output of the encoder 26 is performed, and further, in step S304, it is determined whether or not the pedal section 21 has reached the bending starting position set beforehand. When it is not determined that the pedal section 21 has reached the bending starting position, the process returns to step S302. When, in step S304, it is determined that the pedal section 21 has reached the bending starting position, the leg 3 is in the state SW2, and hence, subsequently in step S306, the stimulation of Ch4 is turned on. Then, in step S308, the sensor information acquisition processing is performed, and in step S310, it is determined whether or not the pedal section 21 has reached the plantar flexion position. When the pedal section 21 has reached the plantar flexion position, the leg 3 is in the state SW3, and in step S312, the stimulation of Ch4 is turned off. At this time, the stimulation of Ch3 is continuously turned on. Then, in step S314, the sensor information acquisition processing is performed, and in step S316, it is determined whether or not the pedal section 21 has reached the bending starting position set beforehand. When it is determined that pedal section 21 has reached the bending starting position, the leg 3 is in the state SW4, and hence, next in step S318, the stimulation of Ch3 is turned off, and the stimulations of Ch1 and Ch2 are turned on.

Next, the process proceeds to step S320 in the routine of FIG. 20, so that the sensor information acquisition processing is performed. Further, in step S322, it is determined whether or not the pedal section 21 has reached the "position set beforehand and corresponding to the position of foot 4 when the heel arrives at the ground surface". When it is determined that the pedal section 21 has reached the dorsiflexion position, the leg 3 is in the state SW5, and hence, in step S324, the intensity of stimulation of Ch2 starts to be gradually reduced. Next, in step S326, the sensor information acquisition processing is performed, and in step S328, it is determined whether or not the pedal section 21 has reached the "position set beforehand and corresponding to the position of the ankle 4a when the sole arrives at the ground surface". When it is determined that the pedal section 21 has reached the plantar flexion position, the leg 3 is in the state SW6, and then, in next step S330, all of the stimulations are turned off. At this time, as shown in FIG. 14, slightly after the stimulation of Ch2 becomes zero, the stimulation of Ch1 becomes zero. Then, in step S332, time is counted until the elapsed time reaches the rest time set beforehand. After the elapse of the rest time, when the leg 3 is in the state SW21, in step S334, Ch1 and Ch2 are turned on to realize the waveform charts showing in FIG. 16. Then, in step S336, the sensor information acquisition processing is performed, and in step S338, it is determined whether or not the pedal section 21 has reached the dorsiflexion position set beforehand. When it is determined that the pedal section 21 has reached the dorsiflexion position, the leg 3 is in the state SW22, and hence, in step S340, all of the stimulations are turned off. Then, in step S342, time is counted until the elapsed time reaches the rest time set beforehand, and after the elapsed time, the number of times of exercise is determined similarly to step S120 of FIG. 17 and FIG. 18. When the integrated number of times of exercise is less than the specified number of times of exercise, the process returns to step S300 of FIG. 19. When the integrated number of times of exercise has reached the specified number of times of exercise, the routine at this time is ended.

In the routine of FIG. 19 and FIG. 20, after states SW1 to SW6, the state is subsequently shifted to SW21 and SW22, and then, from SW1, the same motions are repeated. Thereby, it is realized that the electrical stimulation of the second stimulation pattern B2, the electrical stimulation of the first stimulation pattern A2, the electrical stimulation of the first stimulation pattern A4 are performed, and that the set of these electrical stimulations is repeated. In this case, electrical stimulations of the first and second stimulation patterns are alternately performed in such a way of performing "electrical stimulation of the second stimulation pattern (B2)", "electrical stimulations of the first stimulation patterns (A2 and A4)", "electrical stimulation of the second stimulation pattern (B2)" . . . . Further, in the routine of FIG. 20, according to the position of the pedal section 21, which is based on the output of the encoder 26, turning on and off of the stimulations, and the adjustment of the stimulation intensity, and the like, are performed, but the present invention is not limited to this. Similarly to the stimulation adjustment based on the value of time measurement in the routine of FIG. 18, turning on and off of the stimulations, and the adjustment of the stimulation intensity may also be performed in FIG. 20.

With the specific processes according to the embodiment described above, it is possible that the output signals of the encoder 26 are feed back to the electrical stimulation device 100, so as to adjust the outputs of the electrical stimulation device 100 respectively corresponding to the states SW1 to SW22 in which the states of exercise are respectively set beforehand. It should be noted that the modification, in which the angle sensor, or the like, is provided at the pedal section 21, to accurately detect the dorsiflexion and plantar flexion of the ankle 4a, is preferably applied.

Figure 21:
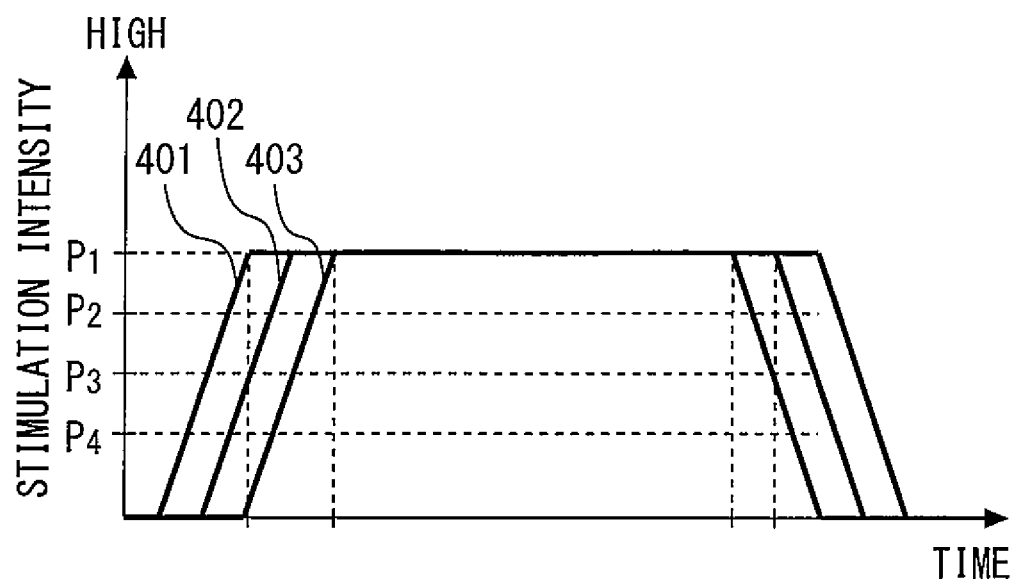
FIG. 21 shows waveform charts showing modification of the electrical stimulation signals according to the embodiment of the present invention.
Figure 22:
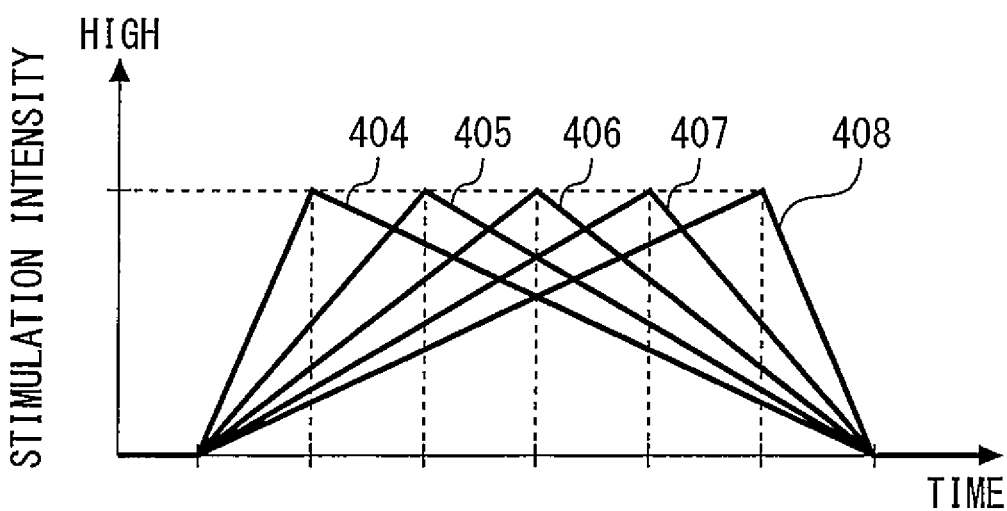
FIG. 22 shows waveform charts showing modification of the electrical stimulation signals according to the embodiment of the present invention.
Figure 23:
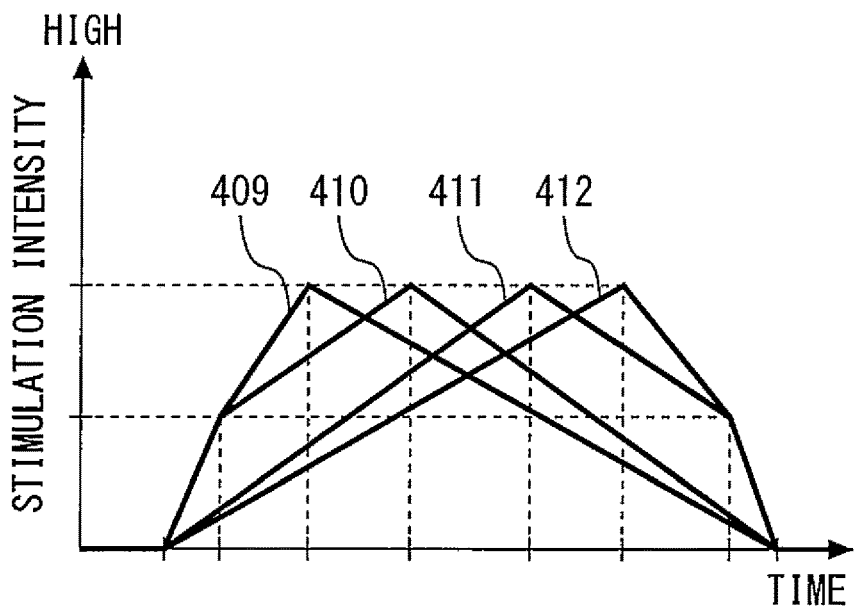
FIG. 23 shows waveform charts showing modification of the electrical stimulation signals according to the embodiment of the present invention.
Figure 24:
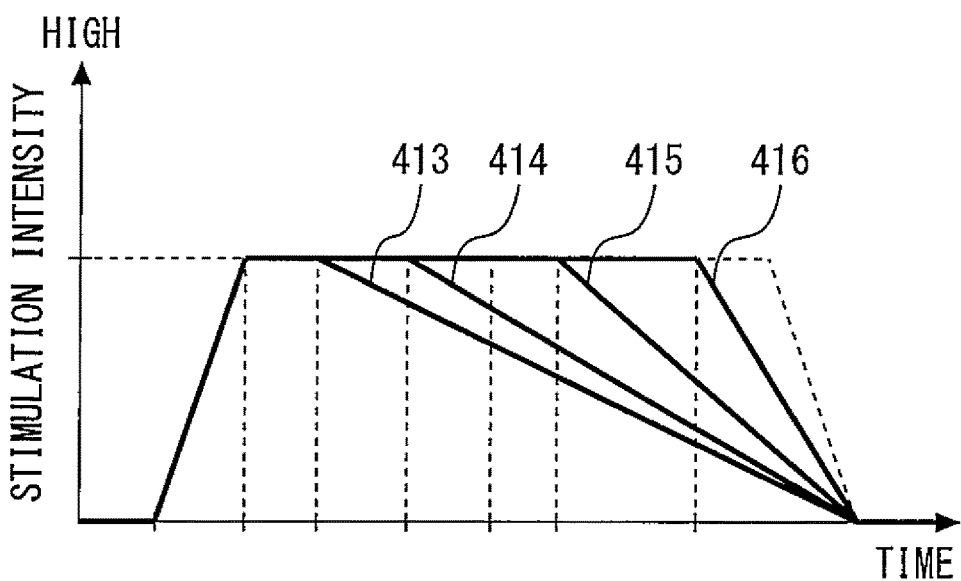
FIG. 24 shows waveform charts showing modification of the electrical stimulation signals according to the embodiment of the present invention.
Figure 25:
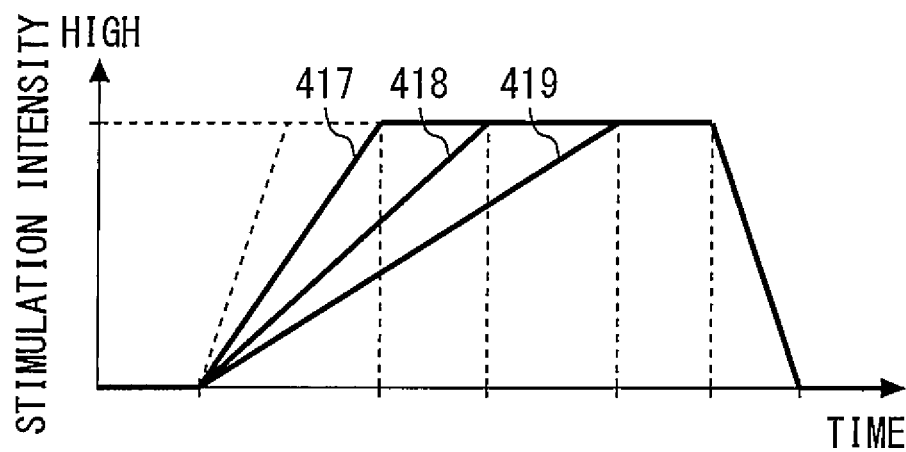
FIG. 25 shows waveform charts showing modification of the electrical stimulation signals according to the embodiment of the present invention.
Figure 26:
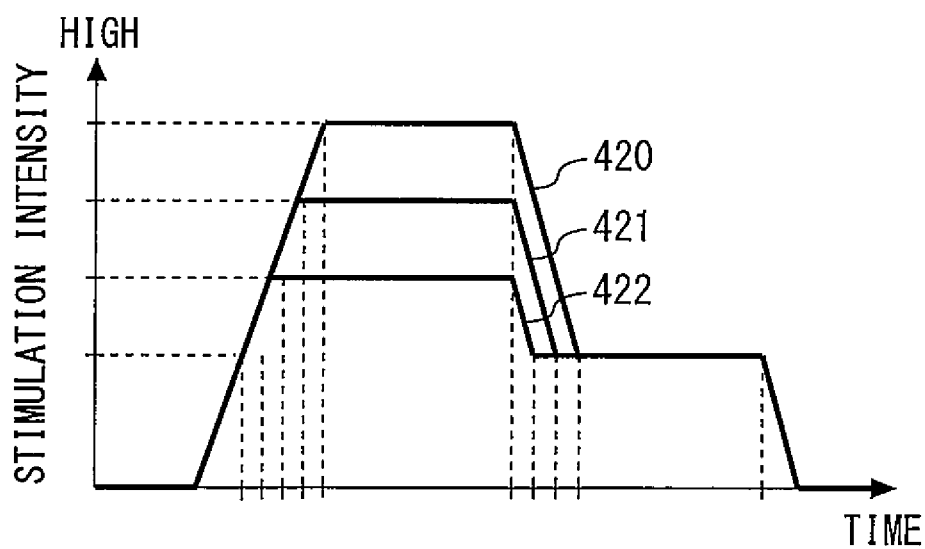
FIG. 26 shows waveform charts showing modification of the electrical stimulation signals according to the embodiment of the present invention.
Figure 27:
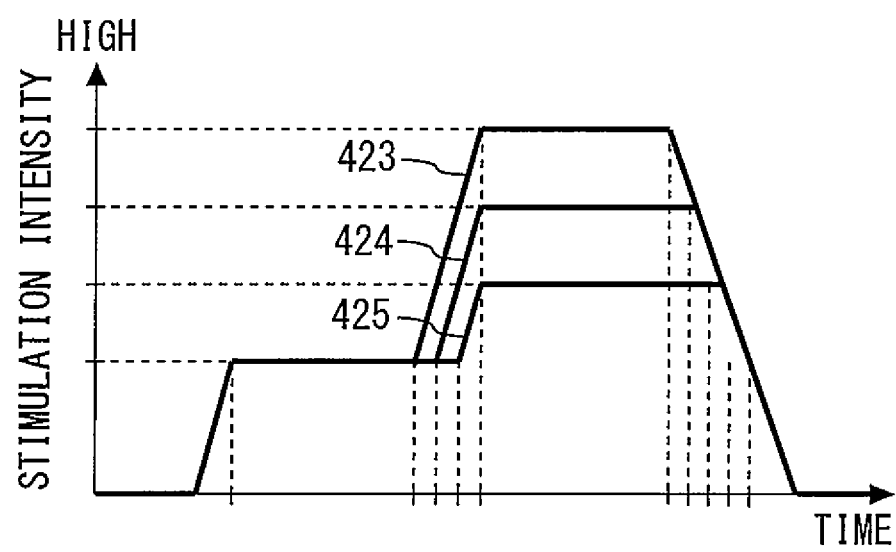
FIG. 27 shows waveform charts showing modification of the electrical stimulation signals according to the embodiment of the present invention.
Figure 28:
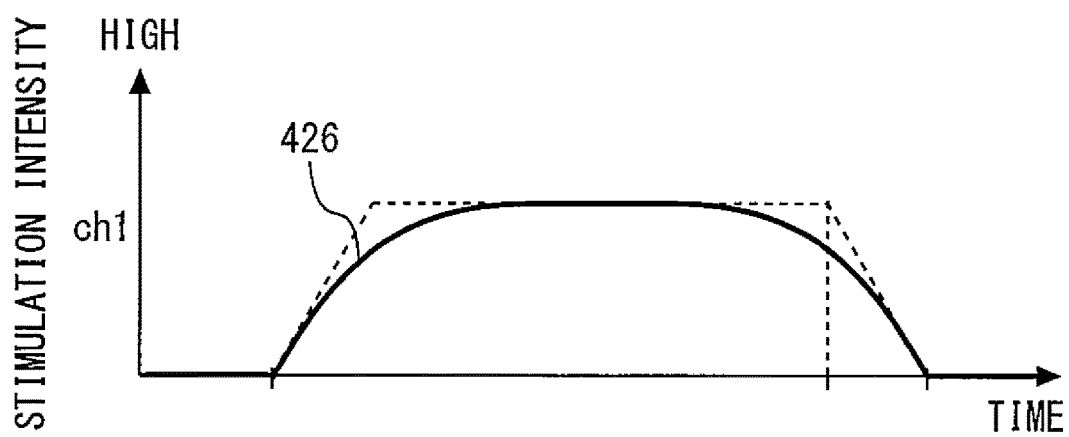
FIG. 28 shows waveform charts showing modification of the electrical stimulation signals according to the embodiment of the present invention.
Figure 29:
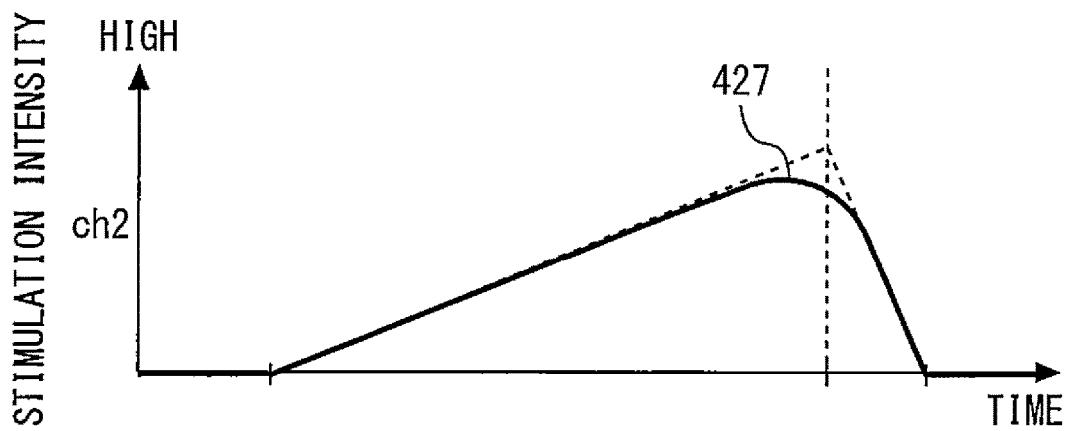
FIG. 29 shows waveform charts showing modification of the electrical stimulation signals according to the embodiment of the present invention.

It should be noted that variations modifications and the possibility of modification are described in the description of the above-described embodiment, but further, the following modifications may be performed. Each of FIG. 21 to FIG. 29 shows waveform charts of modification of electrical stimulation signals according to the embodiment of the present invention, and shows a state where a plurality of waveforms overlap with each other. A waveform, which is selected from groups of following waveforms 401 to 427 and waveforms having shapes equivalent to those of the waveforms 401 to 427, may be applied as the electrical stimulation signals supplied to each of Ch1 to Ch4. The trapezoidal waveforms 401 to 403 having section widths different from each other as shown in FIG. 21 can be applied and the peak value of each of the trapezoidal waveforms 401 to 403 can be selected from peak values P1 to P4. Triangular waveforms 404 to 408 shown in FIG. 22 can be applied, and the triangular waveform 406 having the same increase and decrease rates equal to each other may be applied. Also, the triangular waveforms 407 and 408 in each of which the increase slope is smaller than the decrease slope, or the triangular waveforms 404 and 405 in each of which the increase slope is larger than the decrease slope, may also be applied. As shown in FIG. 23, the waveforms 409 and 410 in each of which the increase slope is formed in two steps, or the waveforms 411 and 412 in each of which the decrease slope is formed in two steps may be applied. However, the number of steps forming the slope is not limited to two and the slope having three or more steps may also be applied. The trapezoidal waveform is not limited to the isosceles trapezoidal waveform as shown in FIGS. 13 to 16, and as shown in FIG. 24 and FIG. 25, trapezoidal waveforms 413 to 419 each having a non-isosceles trapezoidal shape having different trapezoidal legs may be applied. As shown in FIG. 26 and FIG. 27, the waveforms 420 to 422 each of which decreases stepwise or waveforms 423 to 425 each of which increase stepwise may also be applied. As shown in FIG. 28, a waveform 426, which is approximate to the trapezoidal wave as a whole and changes continuously in a curved manner, may be applied. As shown in FIG. 29, the waveform 427, which is approximate to a triangular wave as a whole and changes continuously in a curved manner may also be applied.

It should be noted that, in the present invention, the electrical stimulation process, the control process, the calculation process, the determination process, and other processes, which are described in the present embodiment, may be stored in a CD-ROM, a DVD-ROM, other program storing media, or the like, to be supplied. Further, the processes may be discharged as a simple program. Further, the method for generating the electrical stimulation signals in the above-mentioned embodiment may be performed as the "electrical stimulation method". The control, the analyzing method, and the processes, which are performed by using the exercise apparatus 10 in the above-mentioned embodiment, may be performed as the invention of the "training method".

It should be noted that the present invention is applied to the muscle strength training of the leg 3 in the embodiment, but the present invention is not limited to this. The present invention may be applied to other exercise, for example, the muscle strength training of an arm. Specifically, for example, at the time of holding, picking, and raising an object, an elbow and a wrist are moved in association with each other. Therefore, the electrical stimulation device, the training apparatus, and the electrical stimulation method according to the present inventions can be applied to the muscle strength training of the arm, and in accordance with bending and extension of the elbow, palmar flexion and dorsiflexion of the wrist may be repeatedly performed. For example, the electrical stimulation device 100 is used so that bending and extension of the arm are performed by the stimulations of the electrode pad 110a and the electrode pad 110c, and so that dorsiflexion and palmar flexion of the wrist are performed by the stimulations of the electrode pad 110b and the electrode pad 110d. Further, the exercise detection section 20 in the exercise apparatus 10 may be configured such that the pedal section 21 is configured to be attached to the hand, and is configured such that the direction and length of the rail 23 are changed along the reciprocal linear motion of the hand according to the bending and extension of the arm. In this way, all of the configuration, operations, control, and the like, provided in the training apparatus 1 according to the above-described embodiment, and the modifications of these may apply to the muscle strength training of the arm.

REFERENCE SIGNS LIST 1 training apparatus, 2 exercising person, 3 leg, 3a thigh portion, 3b lower thigh portion, 3c knee, 4 foot, 5a quadriceps femoris muscle, 5b tibialis anterior muscle, 5c biceps femoris muscle, 5d gastrocnemius muscle, 10 exercise apparatus, 20 exercise detection section, 21 pedal section, 21 a pedal body, 21b movable metal fitting, 21ca mat, 21cb mat, 21d metal fitting, 21e rotary shaft, 21f plate, 22 cover, 22a slit, 23 rail, 24 transmission wire, 25 case, 26 encoder, 27 case fixture, 28 control apparatus, 29 top plate, 30 support body, 31 to 37 frame, 40 load generation section, 41 cage section, 42 rail, 43 fixing jig, 44 weight member, 45 cover, 50 attachment belt, 61 cable, 100 electrical stimulation device, 110, 110a to 110d electrode pad, 120 electrical stimulation generation section, 130 power circuit, 130a to 130d power circuit section, 140 adjustment circuit, 140a to 140d adjustment circuit section, 150 controller, 152 memory, 154 input/output circuit, 200 bed, A1 to A4, B1 to B4 stimulation pattern, Ch1 to Ch4 channel

The invention claimed is:

1. An electrical stimulation device comprising:
a first output channel including a pair of electrodes, a second output channel including a pair of electrodes, a third output channel including a pair of electrodes, and a fourth output channel including a pair of electrodes; and
an electrical stimulation generator connected to each pair of electrodes of the first output channel, the second output channel, the third output channel, and the fourth output channel,
wherein the electrical stimulation generator is configured to:
output, via the first output channel, a first electrical stimulation intensity that changes according to a first trapezoidal waveform,
output, via the second output channel, a second electrical stimulation intensity that changes according to a first triangular waveform,
output, via the third output channel, a third electrical stimulation intensity that changes according to a second trapezoidal waveform, and
output, via the fourth output channel, a fourth stimulation intensity that changes according to a combination of a second triangular waveform and a third trapezoidal waveform, wherein the first stimulation intensity and the second stimulation intensity are increased and decreased together, and the third stimulation intensity and the fourth stimulation intensity are increased and decreased together, and
wherein the electrical stimulation generator is further configured to output as a first pair, the first stimulation intensity and the second stimulation intensity, and output as a second pair, the third stimulation intensity and the fourth stimulation intensity alternatively to the first pair.

2. The electrical stimulation device according to claim 1, wherein in at least one of the first triangular waveform and the second triangular waveform, the decrease slope is steeper than the increase slope.

3. The electrical stimulation device according to claim 1, wherein the stimulation supply period of electrical stimulation by the first output channel and the second output channel is longer than the stimulation supply period of electrical stimulation by the third output channel and the fourth output channel.

4. A training apparatus comprising:
an exercise detector configured to detect an exercise state, and
an electrical stimulation device, the electrical simulation device including:
a first output channel including a pair of electrodes, a second output channel including a pair of electrodes, a third output channel including a pair of electrodes, and a fourth output channel including a pair of electrodes; and
an electrical stimulation generator connected to each pair of the electrodes of the first to fourth output channels, the electrical stimulation generator being configured to:
output, via the first output channel, a first electrical stimulation intensity that changes according to a first trapezoidal waveform,
output, via the second output channel, a second electrical stimulation intensity that changes according to a first triangular waveform,
output, via the third output channel, a third electrical stimulation intensity that changes according to a second trapezoidal waveform,
output, via the fourth output channel, a fourth stimulation intensity that changes according to a second triangular waveform that is combined with a third trapezoidal waveform
wherein the first stimulation intensity and the second stimulation intensity are increased and decreased together, and the third stimulation intensity and the fourth stimulation intensity are increased and decreased together,
wherein the device outputs as a first pair' the first stimulation intensity and the second stimulation intensity' and the device outputs as a second pair' of the third stimulation intensity and the fourth stimulation intensity alternately to the first pair, and
wherein, when the exercise state detected by the exercise detector coincides with a pre-set state, an output signal of the exercise detector is fed back to the electrical stimulation generator so as to adjust an output of the electrical stimulation generator.

* * * * *